United States Patent [19]
Mott

[11] Patent Number: 5,500,635
[45] Date of Patent: Mar. 19, 1996

[54] PRODUCTS INCORPORATING PIEZOELECTRIC MATERIAL

[76] Inventor: Jonathan C. Mott, NorthBrook Lodge, Bentley, Farnham, Surrey GU10 5EU, England

[21] Appl. No.: 337,320

[22] Filed: Nov. 10, 1994

Related U.S. Application Data

[63] Continuation of Ser. No. 866,171, filed as PCT/GB91/00267, Feb. 20, 1991, abandoned.

[30] Foreign Application Priority Data

Feb. 20, 1990 [GB] United Kingdom .................... 9003810
May 24, 1990 [GB] United Kingdom .................... 9011681
Jul. 12, 1991 [GB] United Kingdom .................... 9115196

[51] Int. Cl.$^6$ ................................................. G08B 23/00
[52] U.S. Cl. ................... 340/323 R; 340/691; 340/693; 340/665; 340/573; 310/319; 310/328; 310/311; 33/3 A; 33/3 R; 36/137; 374/141
[58] Field of Search .................... 340/323 R, 691, 340/693, 665, 666, 573, 586, 588, 589; 310/319, 339, 311, 328, 337; 33/3 R, 3 A, 3 B; 374/141–143, 183, 185; 36/136, 137; 128/710, 736

[56] References Cited

U.S. PATENT DOCUMENTS 1,597,823  8/1926  Randolph .

(List continued on next page.)

FOREIGN PATENT DOCUMENTS

| 121026A | 10/1984 | European Pat. Off. . |
|---|---|---|
| 0152057 | 8/1985 | European Pat. Off. . |
| 1555306 | 12/1968 | France . |
| 2227714 | 11/1974 | France . |
| 2556190 | 6/1985 | France . |
| 2608485 | 9/1977 | Germany . |
| 489219 | 1/1954 | Italy . |
| 58-195238 | 11/1983 | Japan . |
| 8006456 | 6/1982 | Netherlands . |
| 2121219 | 12/1983 | United Kingdom . |
| WO8102223 | 8/1981 | WIPO . |
| WO8702846 | 5/1987 | WIPO . |

OTHER PUBLICATIONS

BioMechanics VII–B, International Series on BioMechanics, vol. 4B, Proceedings of the 8th International Congress of BioMechanics, Nagoya, Japan 1–1983.

Medical and Biological Engineering and Computing, Foot Force Measuring Device for Clinical Assessment of Pathological Gait, Miyazaki et al., Jul. 1978.

The Complete Handbook of Athletic Footwear, Cheskin, Melvyn P. Fairchild Publications, New York, 1–1987, p. 158.

*Primary Examiner*—Donnie L. Crosland
*Attorney, Agent, or Firm*—Weingram & Zall

[57] ABSTRACT

A product, in particular a shoe, apparel, a ball or a fishing lure, incorporating an impact sensing element made from polymeric piezoelectric material. In response to impact, the piezoelectric material generates an electrical signal to a battery-powered light- or sound-emitting unit or to an information display device which is at least partially molded into or contained in the product, thus causing circuitry to energize the light- or sound-emitting device from the battery or to display information on the information display device. In some embodiments involving light-emitting devices such as LEDs, the light is conducted to an outside surface of the product directly through the LED or via one or more optical fibers. A shoe can be provided with numerous light-emitting devices, one or more impact sensing elements, a temperature sensor and appropriate circuitry to process the impact and temperature information. This information is then used to light appropriate light-emitting devices such as to display a bar graph of temperature or force of impact, to light or flash individual light-emitting devices or to activate an information display device. In addition, a microprocessor can be included in the circuitry to provide preprogrammed control of the light emitting devices or to evaluate the input from the impact sensing element and then light the appropriate light emitting device or devices or to control the information displayed on the information display de2vice.

9 Claims, 19 Drawing Sheets

U.S. PATENT DOCUMENTS

| | | | |
|---|---|---|---|
| 3,239,696 | 3/1966 | Burkhatter et al. | 310/8.6 |
| 3,323,367 | 6/1967 | Searle | 73/379 |
| 3,549,878 | 12/1970 | Bailey | 240/10 |
| 3,580,575 | 5/1971 | Speeth | 273/58 |
| 3,582,691 | 6/1971 | Sonderegger et al. | 310/8.4 |
| 3,582,692 | 6/1971 | Palini | 310/8.5 |
| 3,604,958 | 9/1971 | Palini | 310/8.1 |
| 3,610,916 | 10/1971 | Meehan | 240/6.4 R |
| 3,750,127 | 7/1973 | Ayers et al. | 340/261 |
| 3,798,474 | 3/1974 | Cassand et al. | 310/9.6 |
| 3,828,177 | 8/1974 | Day | 240/6.4 F |
| 3,893,247 | 7/1975 | Dana, III | 36/2.5 K |
| 3,940,868 | 3/1976 | Northcutt | 43/17.6 |
| 3,946,505 | 3/1976 | Dana, III | 36/2.5 K |
| 3,974,491 | 8/1976 | Sipe | 340/272 |
| 4,020,572 | 5/1977 | Chiaramonte, Jr. | 36/137 |
| 4,054,808 | 10/1977 | Tanaka | 310/323 |
| 4,112,601 | 9/1978 | Chiaramonte, Jr. | 36/137 |
| 4,128,861 | 12/1978 | Pelengaris | 362/103 |
| 4,130,951 | 12/1978 | Powell | 36/137 |
| 4,158,117 | 6/1979 | Quilliam et al. | 200/181 |
| 4,158,922 | 6/1979 | Dana, III | 36/137 |
| 4,216,403 | 8/1980 | Krempl et al. | 310/328 |
| 4,250,650 | 2/1981 | Fima | 43/17.6 |
| 4,253,253 | 3/1981 | McCormick | 36/137 |
| 4,304,126 | 12/1981 | Yelke | 73/119 A |
| 4,328,441 | 5/1982 | Kroeger, Jr. et al. | 310/319 |
| 4,347,681 | 8/1982 | Fima | 43/17.6 |
| 4,402,147 | 9/1983 | Wu | 36/136 |
| 4,499,394 | 2/1985 | Koal | 310/330 |
| 4,510,704 | 4/1985 | Johnson | 36/136 |
| 4,595,200 | 5/1986 | Shishido | 273/58 |
| 4,660,305 | 4/1987 | Medler et al. | 36/139 |
| 4,703,217 | 10/1987 | Ratzlaff et al. | 310/338 |
| 4,703,445 | 10/1987 | Dassler | 364/561 |
| 4,737,134 | 4/1988 | Rumsey | 446/409 |
| 4,741,120 | 5/1988 | Cota et al. | 43/17.6 |
| 4,747,413 | 5/1988 | Bloch | 374/110 |
| 4,748,366 | 5/1988 | Taylor | 310/328 |
| 4,771,394 | 9/1988 | Cavanagh | 364/561 |
| 4,814,661 | 3/1989 | Ratzlaff et al. | 310/328 |
| 4,824,107 | 4/1989 | French | 273/1 GC |
| 4,848,009 | 7/1989 | Rogers | 36/137 |
| 4,991,150 | 2/1991 | Wixom | 367/147 |
| 5,033,212 | 7/1991 | Evanyk | 36/137 |
| 5,065,067 | 11/1991 | Todd et al. | 310/319 |
| 5,188,447 | 2/1993 | Chiang et al. | 362/103 |

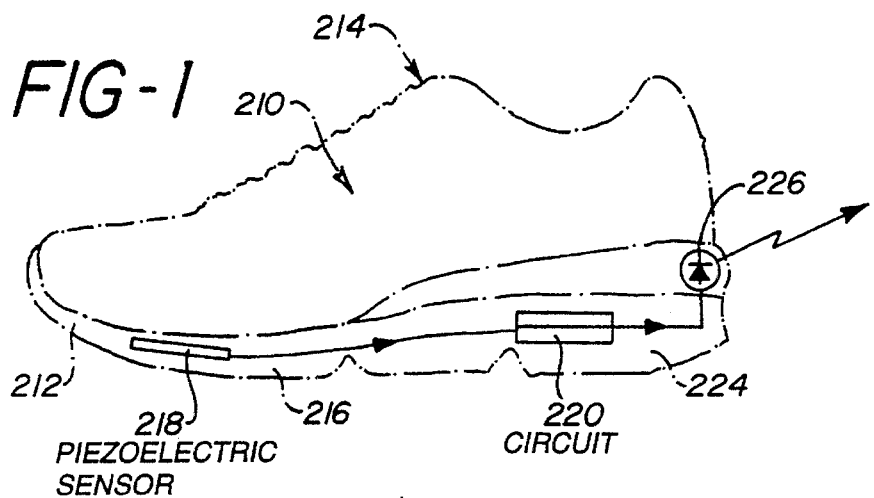
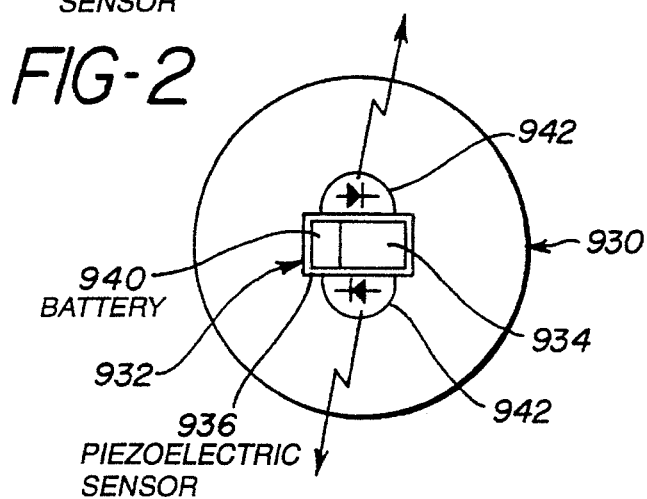
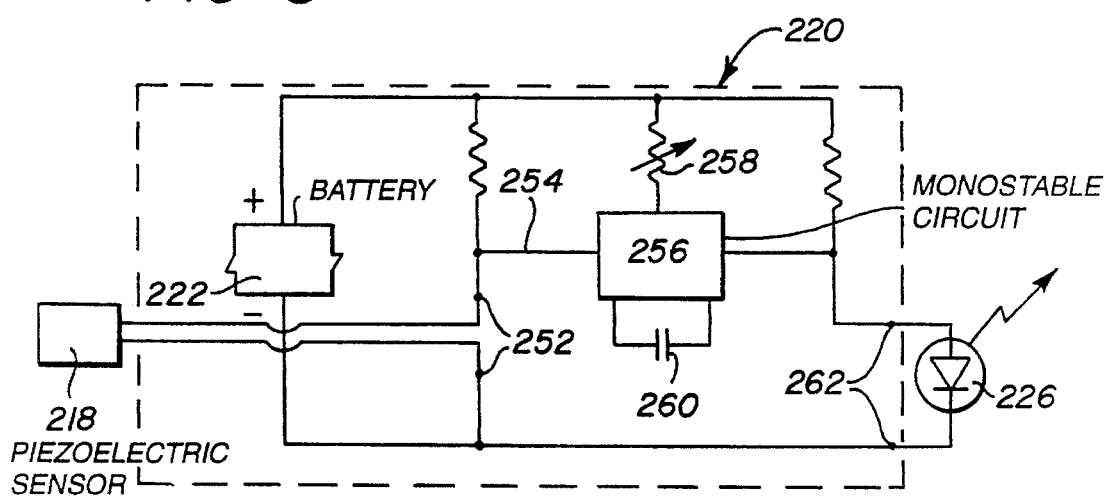

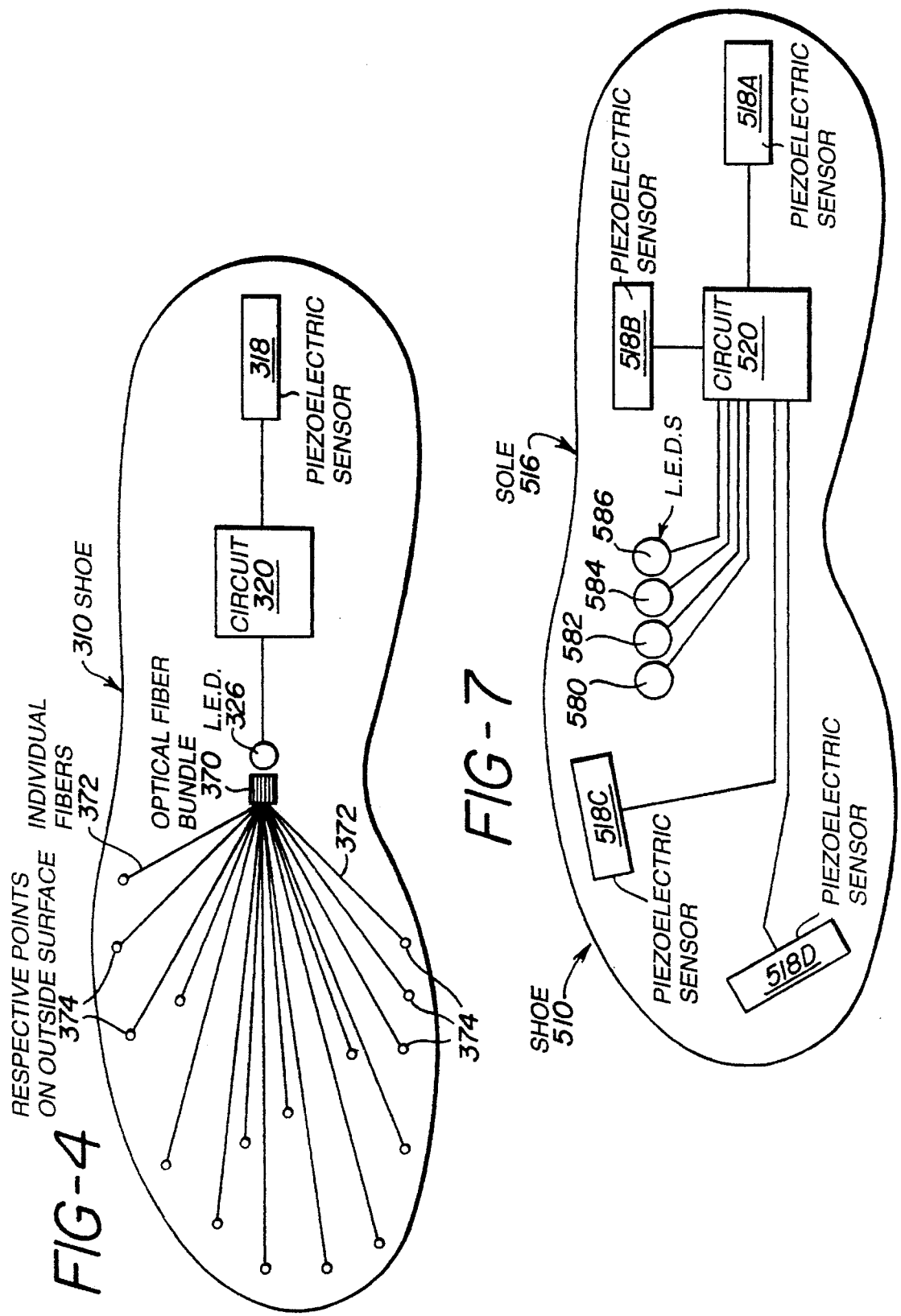

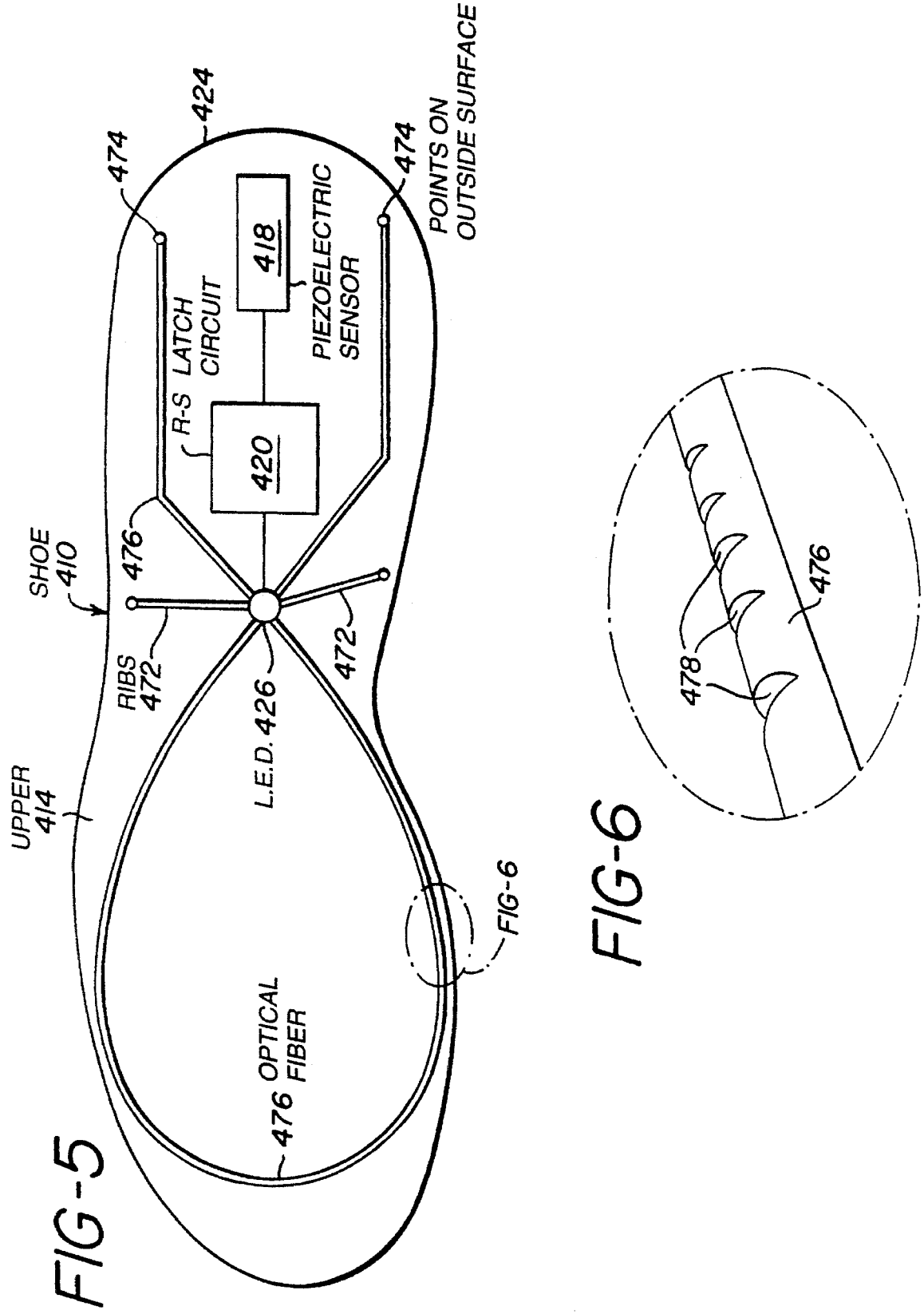

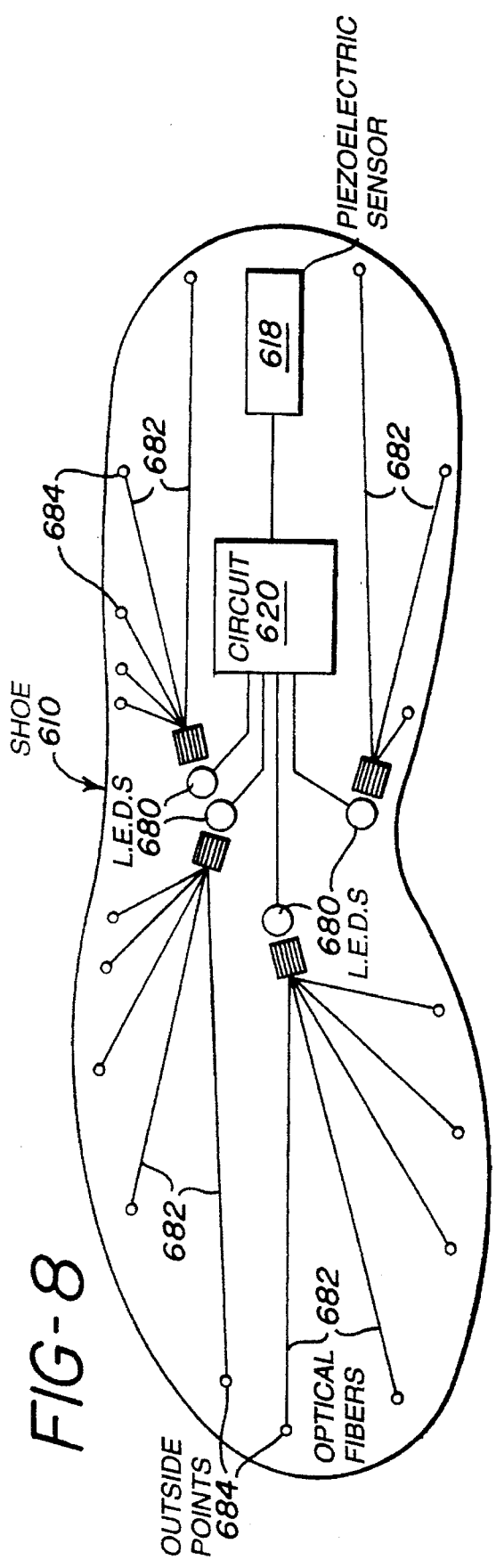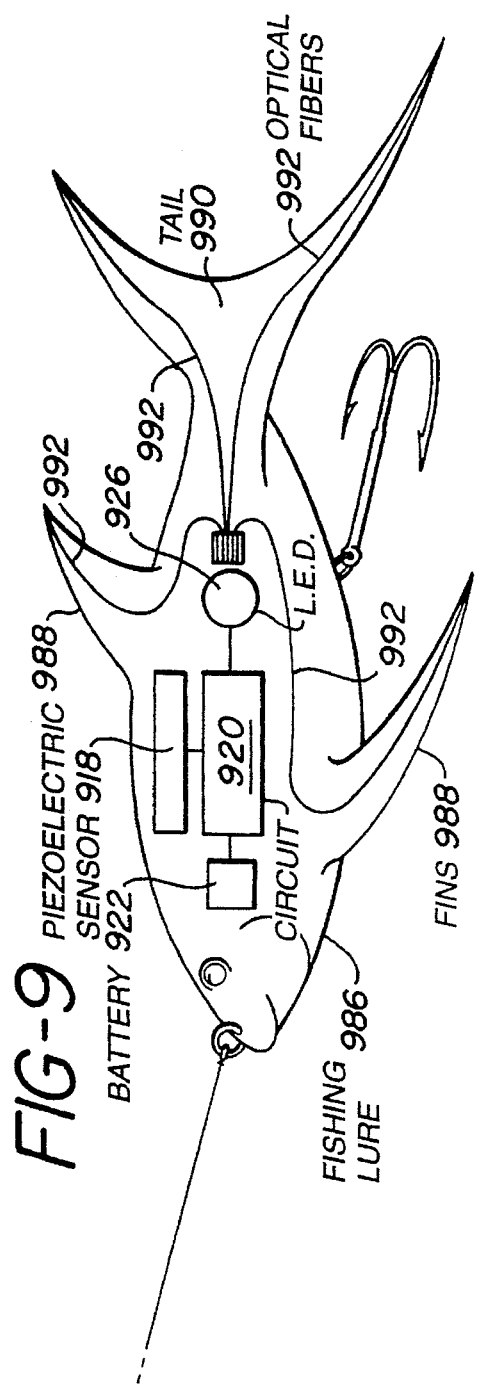

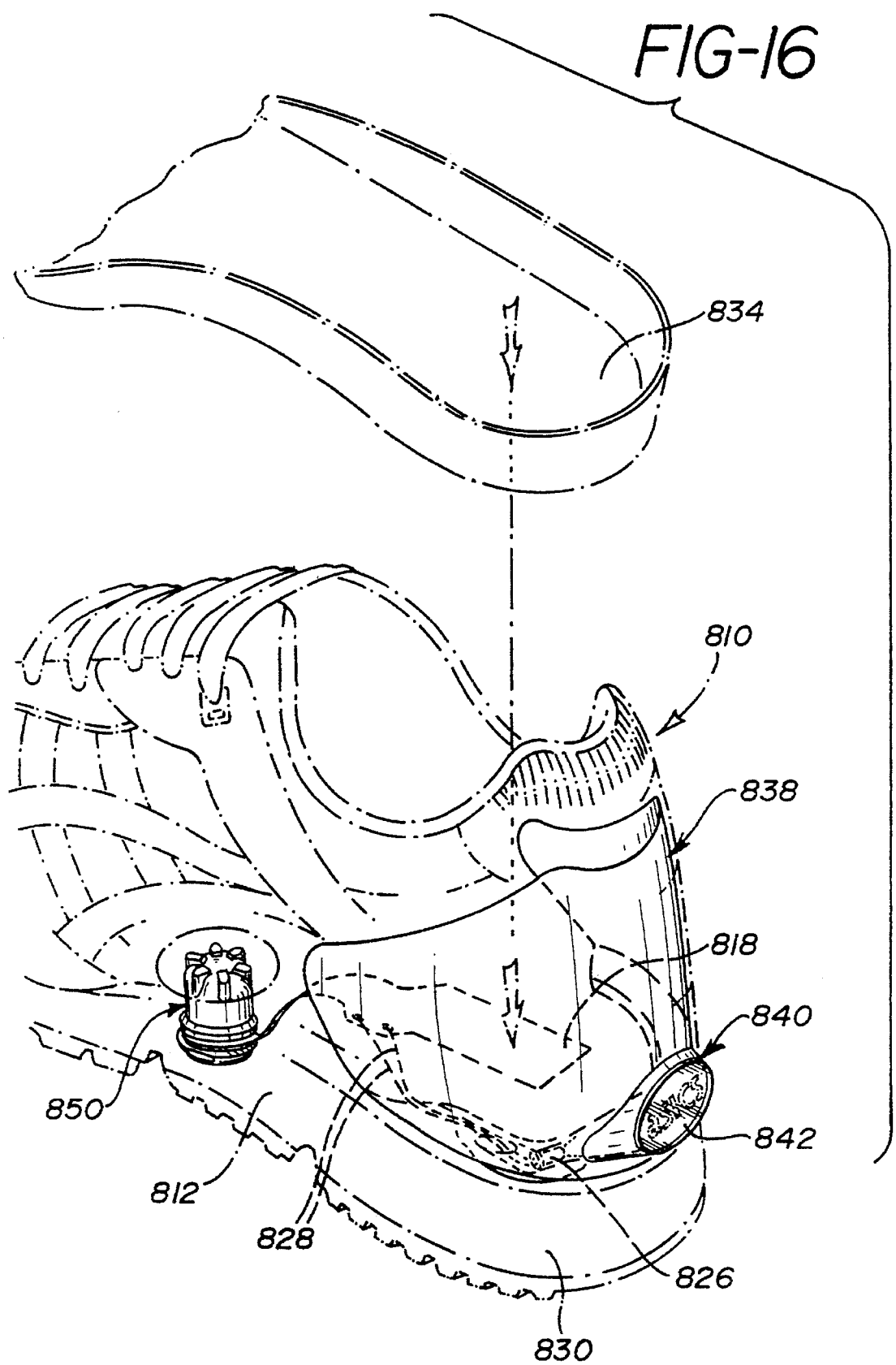

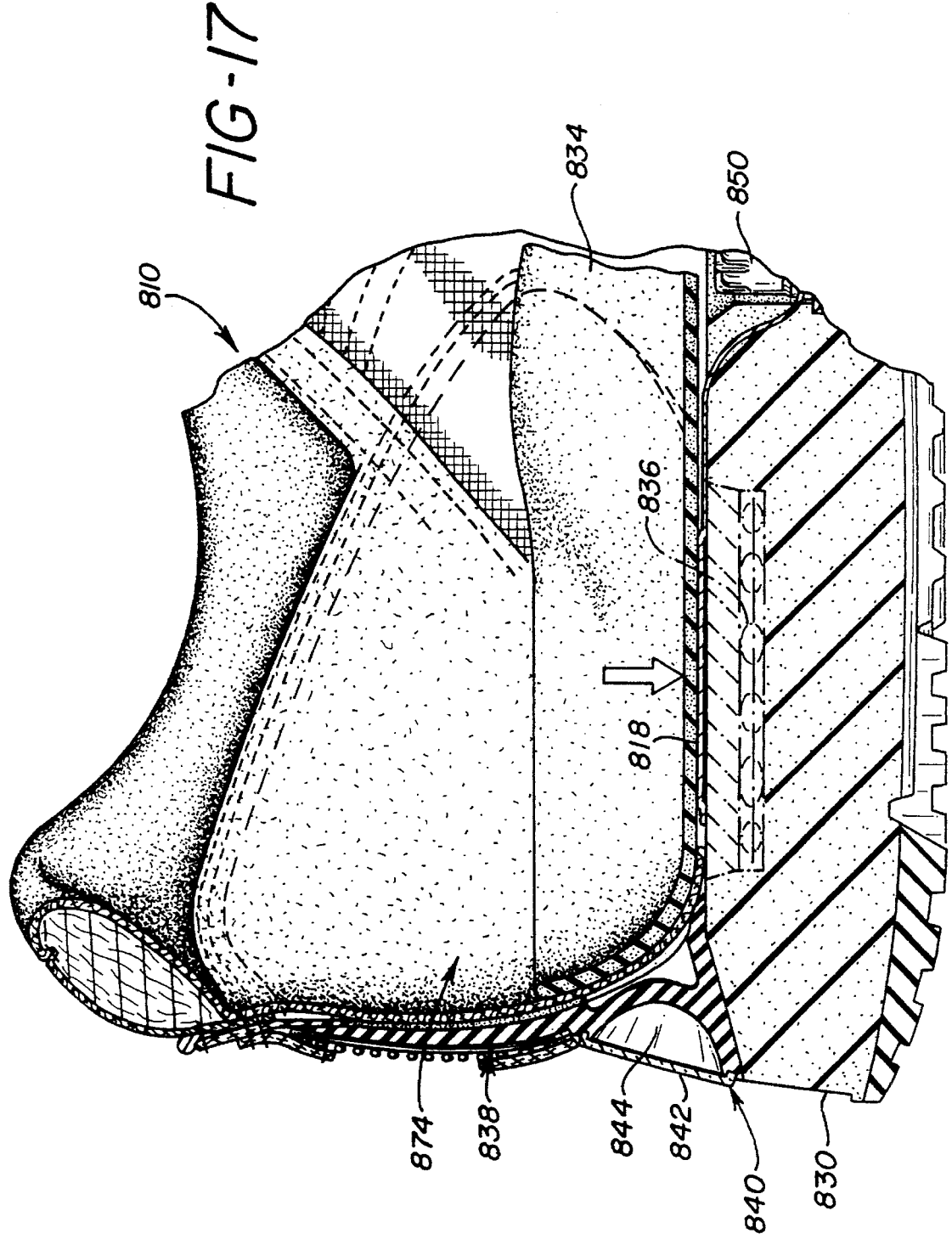

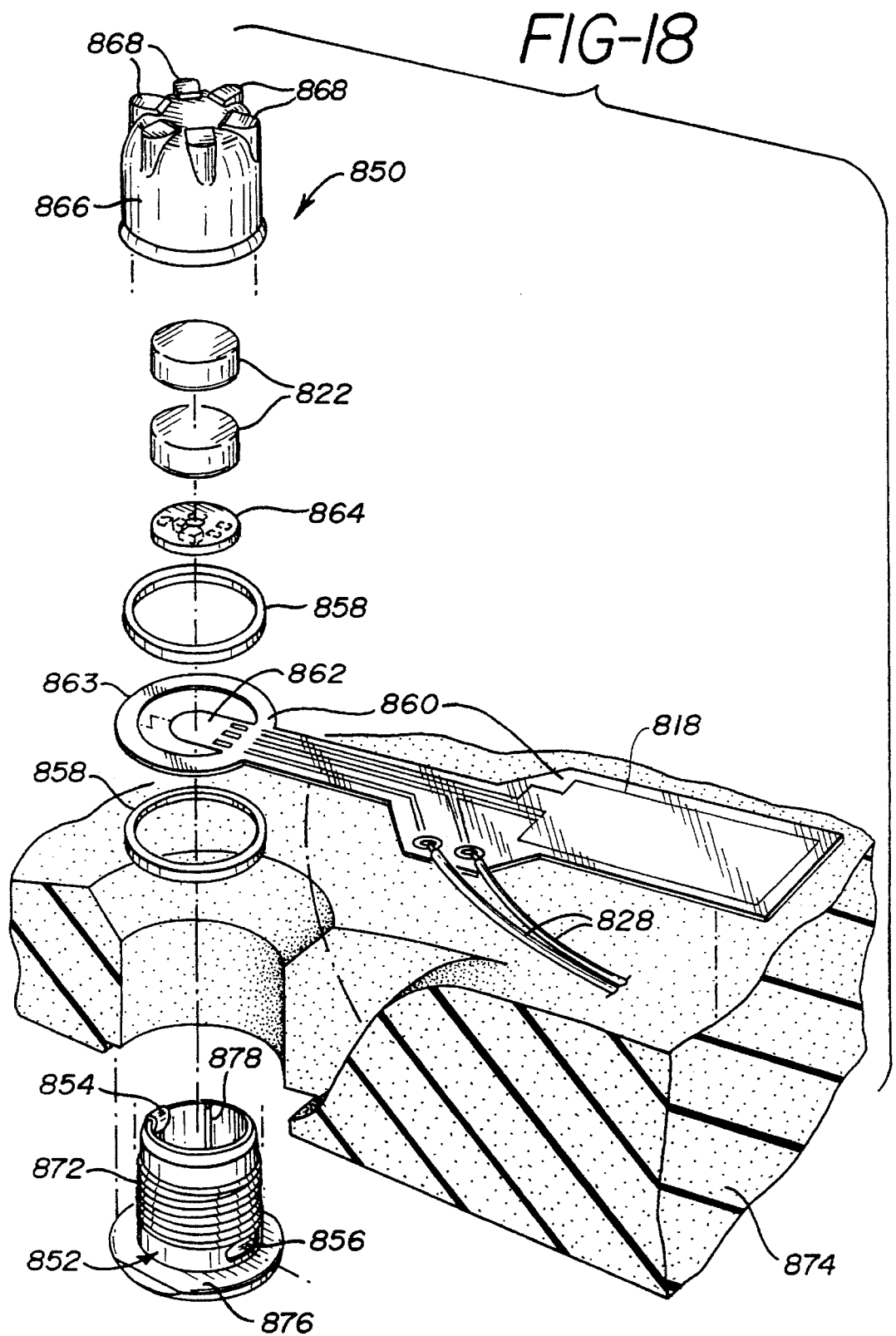

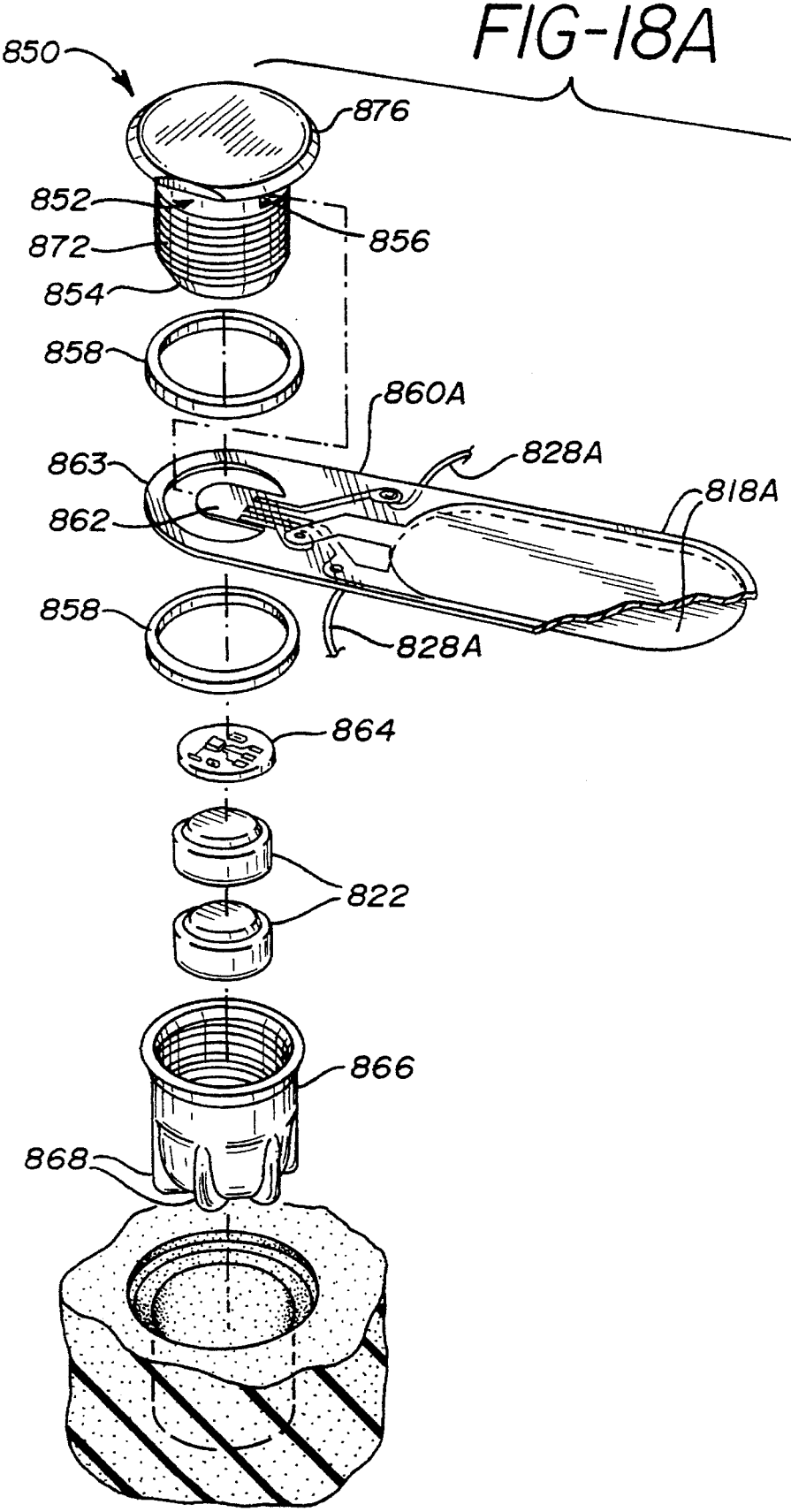

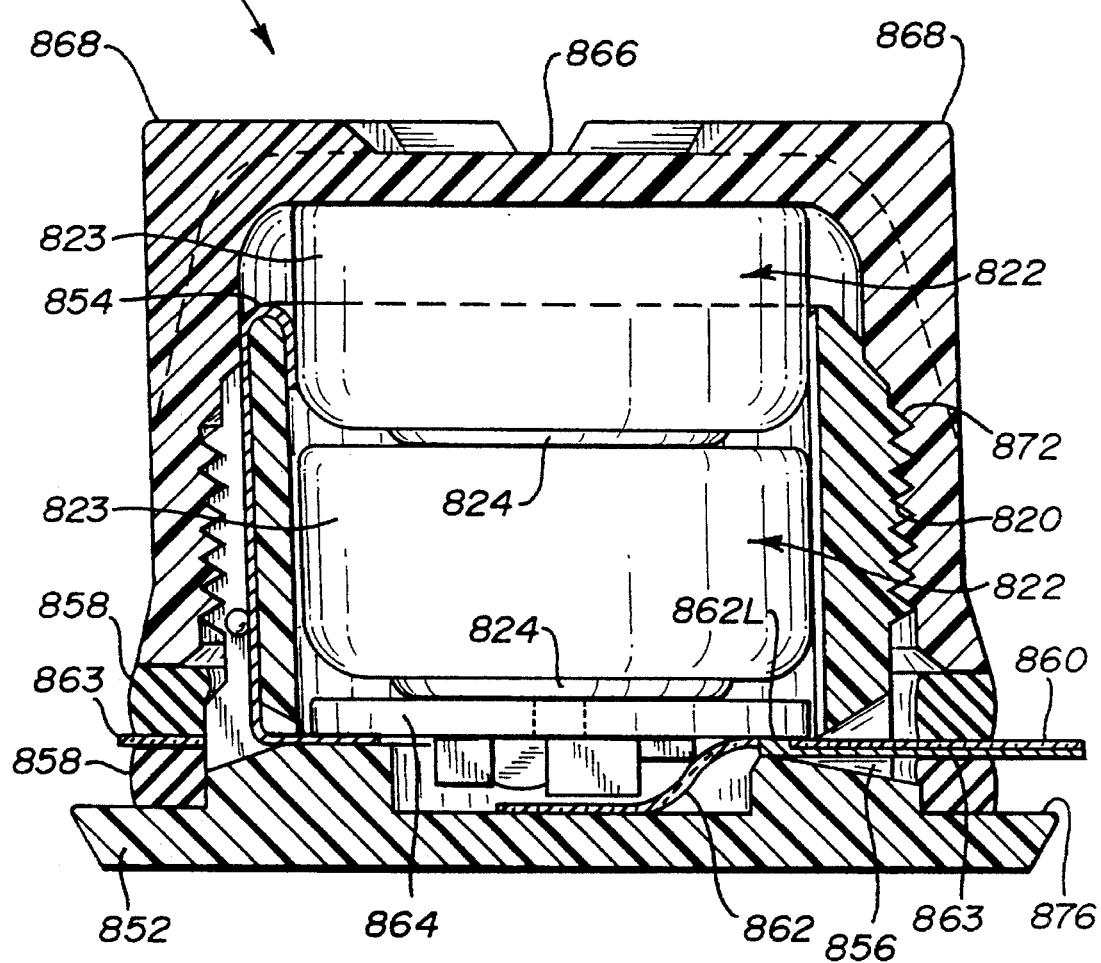

PRODUCTS INCORPORATING PIEZOELECTRIC MATERIAL

RELATED APPLICATION

This is a continuation of application Ser. No. 07/866,171 filed on Jun. 26, 1992 now abandoned.

This is a continuation in part application of PCT Application Serial No. PCT/GB91/00267 having an International Filing Date of Feb. 20, 1991, which claims priority of United Kingdom Application 9003810.0 filed Feb. 20, 1990, and United Kingdom Application 9011681.5 filed May 24, 1990. This application also claims priority of United Kingdom Application No. 9115196.9, filed Jul. 12, 1991.

BACKGROUND OF THE INVENTION

1. Field of the Invention

This invention relates to products incorporating piezoelectric material, and is more particularly but not exclusively concerned with such products in the form of sports shoes, balls and fishing lures.

2. Prior Art

It has already been proposed, for example in U.S. Pat. No. 4,748,366 to Taylor, to provide dancing shoes and a child's ball each incorporating a layer of piezoelectric material and a light source. The piezoelectric material and the light source are directly electrically connected together so that the electrical energy produced by the piezoelectric effect upon impact of the shoe or ball against the ground or other surface, directly energizes the light source.

However, the amount of electric energy normally produced in response to a typical impact is insufficient to produce readily visible energization of the light source, i.e. energization of the light source which is clearly visible in daylight and/or of significant duration.

Numerous U.S. references describe lighted shoes, shoes incorporating piezoelectric materials, other articles incorporating piezoelectric materials and pressure sensitive articles, see, for example the following:

U.S. Pat. No. 1,597,823 to Randolph discloses a shoe having an illuminating means disposed within the heel thereof. The illumination means is controlled by a manual switch mechanism. U.S. Pat. No. 3,239,696 to Burkhalter, et al. discloses a piezoelectric pressure transducer that responds to pressure variations ranging from subaudio frequencies into, at least, the audio range. The transducer is used in sphygmomanometry to measure the systolic and the diastolic limits of blood pressure variation and for other medical applications.

U.S. Pat. No. 3,323,367 to Searle discloses a grip indicator for measuring the pressure exerted by a player on a club or racquet. The grip indicator comprises one or more sensors whose electrical resistance changes when compressed and a meter and bridge circuit to measure this change.

U.S. Pat. No. 3,549,878 to Bailey. discloses a light distribution system for distributing a pattern of light over the clothing of a wearer. In a typical embodiment, plunger-type switches are mounted in various locations in the shoes of a wearer. Pressure imparted to various parts of the shoes, as in dancing, activates these switches. These switches, in turn, activate corresponding switches which control the amount of current applied to a piezoelectric spiral. Variations in the current applied to this spiral cause the spiral length to increase thereby rotating the tip of the spiral. This rotational motion of the spiral tip is used to control the rotation of a multicolor light filter and thus change the pattern of light produced.

U.S. Pat. No. 3,582,691 to Sonderegger, et al. discloses a force transducer unit comprising piezoelectric elements mounted so as to divide the external forces applied into exactly defined partial forces.

U.S. Pat. No. 3,582,692 to Palini discloses an improved piezoelectric transducer responsive to changes in pressure and a circuit for activating a reed relay. The transducer includes a piezoelectric element, a pair of electrodes on opposite sides of the element, means for supporting the element, and an actuator means connected to the element for applying pressure to the element.

U.S. Pat. No. 3,604,958 to Palini discloses a transducer for use in a security device to protect objects from unauthorized removal. The device senses both increases and decreases in pressure and provides an output signal indicating pressure changes. The transducer includes a piezoelectric element and an actuator for transmitting pressure to the piezoelectric element. When either an increase or decrease in pressure occurs, the piezoelectric element produces an output signal. This output signal decreases the conductivity of a unidirectional current device which then activates a warning circuit.

U.S. Pat. No. 3,750,127 to Ayers, et al. discloses a piezoelectric sensor used as a strain gauge, an intrusion detector, or a thermal gradient detector. The piezoelectric sensor produces an electrical signal proportional to the amount of strain or deformation sensed.

U.S. Pat. No. 3,798,474 to Cassand, et al. discloses a pressure wave sensor having a piezoelectric element with two faces. Each face is associated with a flexible conducting electrode over the entire length of the sensitive element. The sensor may be used for measuring pressure variations resulting from seismic vibrations in the sea or on the earth.

U.S. Pat. Nos. 3,893,247 and 3,946,505 to Dana, III disclose shoes having illuminated sole and heel portions. A battery circuit and lamp source are located in the heel and/or sole of the shoe. The lamp is turned on and off by a tilt switch and/or a manually actuated switch.

U.S. Pat. No. 3,974,491 to Sipe discloses a device for activating a buzzer when a predetermined load is placed on one's foot. The device comprises a resilient liquid-filled tube mounted within a foot pad, the tube extending from adjacent the toe end of the foot pad to adjacent the heel end. Pressure on the liquid compresses a spring which at a predetermined pressure causes the buzzer to activate.

U.S. Pat. No. 4,020,572 to Chiaramonte, Jr. discloses a shoe platform having an illuminated sole. A lamp circuit and battery are located in the platform and controlled by a manual switch.

U.S. Pat. No. 4,054,808 to Tanaka discloses a vibration detecting device for use with musical instruments for detecting vibrations therein. The device comprises a structure containing a piezoelectric ceramic plate housed in a case.

U.S. Pat. No. 4,112,601 to Chiaramonte, Jr. discloses a shoe having a high-intensity lamp, a battery, a light modulator and filters for emitting a sequence of colored light from the lamp. The colored light is emitted through a light transmitting material comprising the riser of the shoe.

U.S. Pat. No. 4,128,861 to Pelengaris discloses an illuminated shoe having a lamp and battery circuit disposed within the heel of the shoe and a means for activating the lamp comprising contacts on the heel of the shoe. Upon application of pressure to the heel, these contacts are pressed together, the battery circuit closes and causes the lamp to light.

U.S. Pat. No. 4,130,951 to Powell discloses an illuminated dancing shoe having an flashlight mounted in the heel and a bundle of optical fibers which extend from the flashlight through the sole to various points around the edge of the sole. The flashlight is turned on and off by a spring operated pressure switch. This switch turns on the flashlight when the wearer applies pressure to the heel of the shoe such as by resting or tapping the heel on the dance floor.

U.S. Pat. No. 4,158,117 to Quilliam, et al. discloses a pressure sensitive switch that includes a polyvinylidene fluoride sheet polarized to render it piezoelectric and a manual push button. Pressing the push button compresses the polyvinylidene fluoride sheet which then generates an electrical signal.

U.S. Pat. No. 4,158,922 to Dana, III discloses a lighted shoe wherein a built-in solid state oscillator (or a tilt switch) and battery circuit flashes a lamp so as to light the transparent portion.

U.S. Pat. No. 4,216,403 to Krempl, et al. discloses a transducer having a piezoelectric measuring sensor element for measurement of mechanical values on hollow bodies, especially pressure distribution within pipes.

U.S. Pat. No. 4,253,253 to McCormick discloses an ornamental shoe having a transparent heel with a battery circuit and a lamp. When the lamp is turned on, it lights the transparent heel. U.S. Pat. No. 4,304,126 to Yelke discloses a transducer for sensing and monitoring the injection of fuel into a fuel injection engine. The transducer includes a piezoelectric element mounted on the fuel line to sense the change in the circumferential dimension of the line due to pressure surges in the line.

U.S. Pat. No. 4,328,441 to Kroeger, Jr., et al. discloses a pressure sensitive apparatus for producing electrical signals on two electrodes. The apparatus includes a conductive layer, a piezoelectric polymer film layer, an electrode layer, an insulating layer, another electrode layer, another piezoelectric polymer film layer and another conductive film layer. This reference teaches the use of both high impedance voltage sensing interface circuits and low impedance current sensing interface circuits to process the signal output by a piezoelectric sensor.

U.S. Pat. No. 4,402,147 to WU discloses an electronic counter mounted in the toe of a shoe which counts the number of steps taken. Contact switches that close when walking a step activate counter circuitry which then causes a digital display to either count up or count down.

U.S. Pat. No. 4,499,394 to Koal discloses a piezoelectric sensor attached to the foot of an animal to continuously measure the pressure of the animal's foot against a reactive surface. The sensor and associated circuitry is electrically interconnected with telemetry and analyzing apparatus.

U.S. Pat. No. 4,510,704 to Johnson discloses a mechanical or electronic pedometer which is contained in the heel of a shoe. The pedometer detects when a step is taken. In the electronic counting embodiment, the pedometer includes electronic counting and processing circuitry, a battery, an impulse transducer (i.e. a piezoelectric element) to trigger a count, and an electronic display of the total count.

U.S. Pat. No. 4,660,305 to Medler, et al discloses a tap dance shoe wherein impact sensors including piezoelectric transducers are contained in the taps attached to the dance shoe. The sensor produces an electrical signal when the tap strikes the dance floor. This electrical signal is then transmitted for remote processing and amplification.

U.S. Pat. No. 4,703,217 to Ratzlaff, et al discloses a piezoelectric transducer mounted on a horseshoe to enable measurement of the forces generated when a horse's hoof contacts the ground. The signal from the piezoelectric transducer is amplified and processed by electronic circuitry so that its information content can be stored and used in scientific studies of a locomotion pattern.

U.S. Pat. No. 4,778,366 to Taylor discloses novel uses of piezoelectric materials for creating optical effects which are directly powered by the electrical energy generated by the piezoelectric materials. The piezoelectric material is incorporated into an article manufacture such that by using the article, mechanical energy is imported to the piezoelectric material, thus causing the generation of an electrical voltage. The voltage is tranferred to an optical effect device which can be activated by the high voltage, low current output of the piezoelectric material. Such devices include electroluminescent materials, gas discharge (plasma) panels, neon bulbs and liquid crystal devices. The output of the piezoelectric material is directly coupled to the optical effect device. This reference also teaches the use of layers of piezoelectric material to generate the energy required to activate the optical effect.

U.S. Pat. No. 4,771,394 to Cavanagh discloses a pair of running shoes provided with a housing at the heels in which an electronic footstrike counting device may be removably mounted thereon. The electronic device is cabled to a computer before and/or after usage of the shoes to transfer footstrike count and run time data to the computer or to have the computer preprogram the electronic device with distance data so that when a given distance is completed, a tone will sound. The electronic device includes an inertia switch for producing a foot strike count. U.S. Pat. No. 4,814,661 to Ratzlaff, et al. discloses a system for measuring and analyzing the forces exerted during running or walking. The system includes piezoelectric sensor elements mounted on a plate which may or may not be incorporated into a shoe. The plate extends under all or portions of the plantar surfaces of a human foot to provide accurate foot force detection during unrestrained motion.

U.S. Pat. No. 4,824,107 to French discloses a martial arts sports scoring device wherein piezoelectric film is mounted on protective equipment such as headgear, handgear or footgear, protective vests and the like. The piezoelectric film produces an electrical signal with an amplitude corresponding to the force of a blow or the degree of deformation of the film. The electrical signal can be processed by electronic circuitry to count the number of blows or to measure the amount of force of each blow. The results of this analysis can be displayed on various types of displays including meters or a bar of light emitting diodes, or these results can be converted into audible tones.

U.S. Pat. No. 4,848,009 to Rogers discloses footwear having a motion responsive switch, a battery, a timing circuit, and a lamp, preferably a light emitting diode. This reference teaches using a motion responsive mercury switch that alternates states in response to the motion of the footwear. When the motion causes the switch to activate (ON), a timing circuit is activated and the lamp is lit. After a predetermined time, the timing circuit turns off the lamp and prevents the lamp from being turned on again until the motion responsive switch makes an OFF transition and then an ON transition. Thus this reference teaches turning a lamp ON again only in response to a change in orientation of the footwear after the timing circuit times out. This reference does not teach lighting a lamp in response to pressure or impact on a sensor embedded in an athletic shoe.

U.S. Pat. No. 4,991,150 to Wixom discloses a dynamic mechanical stress transducer comprising a piezoelectric material in intimate electrical communication with an electroluminescent material that emits light at an intensity in proportion to the magnitude and rate of change of the stress applied to the piezoelectric material. In a preferred embodiment, the electroluminescent material comprises a light emitting diode.

References uncovered relating to toys, for example balls, are:

U.S. Pat. No. 3,580,575 to Speeth discloses an impact toy, such as a ball, with a circuit, impact operated switches and three colored lamps mounted in the interior. Upon impact of the toy, one of the three switches closes and a corresponding lamp lights.

U.S. Pat. No. 3,610,916 to Meehan discloses an illuminable ball with an inertia switch and a time delay circuit. The ball is translucent and within the ball is an inertia switch which triggers a time delay circuit that then applies battery power to two lamps. Power is applied for a duration preselected by the time delay circuit.

U.S. Pat. No. 4,595,200 to Shishido discloses a sound emitting ball. In one embodiment, the external impact force is detected by a piezoelectric sensor which triggers electronic processing and amplification circuitry. This circuitry then causes a piezoelectric speaker to emit a buzzer sound or a melody sound.

U.S. Pat. No. 4,737,134 to Rumsey discloses a ball that produces audible tunes corresponding to the amount of light that falls upon a light transducer mounted on the surface of the ball. An oscillator is coupled to the light transducer and to a speaker to produce the tones. A motion switch turns off the audible tone when the ball is at rest for a preset time period.

References uncovered relating to fishing lures are:

U.S. Pat. No. 3,828,177 to Day discloses a fishing lure having a battery and a lamp disposed therein. A bundle of optical fibers extends from the lamp to the exterior of the lure to conduct light to the outside of the lure.

U.S. Pat. No. 3,940,868 to Northcutt discloses a fishing lure having a battery and a light emitting diode that is turned on by a water activated switch.

U.S. Pat. Nos. 4,250,650 and 4,347,681 to Fima discloses a fishing lure containing one or more lamps and a guideway along which a battery rolls as the lure moves. Movement of the battery along the guideway intermittently completes a lamp circuit and turns on the lamps. The light from these lamps is transmitted by optical fibers to the surface of the lure.

U.S. Pat. No. 4,741,120 to Cota, et al discloses a self-illuminating fishing lure having a constant light source produced by a tritium capsule encapsulated within a hard translucent fish lure body.

Foreign references uncovered relating to this invention are:

Italian Patent No. 489,219 to Valentino discloses a shoe with an on/off switch and a lamp in the heel which illuminates the heel.

French Patent No. 1,555,306 to Deus, et al. discloses an illuminated shoe having a piezoelectric transducer, which when compressed, lights a lamp.

French Patent No. 2,227,714 to Rich discloses a shoe with an illuminated heel having a battery, a mercury switch, a relay and a lamp arranged within the heel so that when the shoe is in a flat position, the lamp is turned off.

French Patent No. 2,556,190 to Hume discloses a shoe having a battery powered flashing lamp in the heel. Lamp current passing through a bimetallic switch heats the switch thereby opening the lamp circuit; the bimetallic switch then cools and closes the lamp circuit, thus causing flashing of the lamp.

Netherlands Pat. No. 8006456 to Maria De Nijs, et al. discloses a battery circuit, a switch, a lamp or light emitting diode, a colored bead, and an optical fiber interconnecting the lamp with the colored bead.

Japanese Application No. 58-195238 to Daitou discloses an electro-mechanical transducer comprising a high polymer film having localized piezoelectric properties. This transducer may be used as a contactless keyboard.

European Patent Application No. 83 307822.3 to Dana III discloses a shoe having a lamp or light emitting diode, a battery circuit and a mercury switch or a mechanically activated pressure switch to light or flash the lamp. Flasher circuitry can be added which is manually activated by the wearer. In addition, the flasher circuits and battery can be encapsulated.

German Patent No. 26 08 485 to Ben-Hassine discloses an illuminated shoe heel having a battery circuit and a mercury switch for turning on and off a plurality of lamps or light emitting diodes mounted through the surface of the shoe heel. The mercury switch turns off the lamps when the heel is raised.

International Application No. PCT/AU86/00324 to Hopper discloses a touch or proximity switch that incorporates a light emitting diode to visually indicate the on or off state of the switch. A piezoelectric stress sensor may be used to trigger circuitry that lights the light emitting diode and to trigger a solid state switch or a transistor.

PCT/US80/01677 to Kroeger, Jr., et al. discloses a pressure sensitive apparatus for producing electrical signals on two electrodes. The apparatus comprises a layered structure including a conductive layer, a piezoelectric polymer film layer, an electrode layer, an insulating layer, another electrode layer, another piezoelectric polymer film layer and another conductive layer. Kroeger teaches the use of a high-impedance interface such as a digital gate or an operational amplifier circuit to sense the voltage generated by the pressure sensitive piezoelectric sensor.

Other references uncovered are:

Biomechanics VII-B, International Series on Biomechanics, Volume 4B, Proceedings of the Eighth International Congress of Biomechanics, Nagoya, Japan, 1983, discloses a shoe having an array of piezoelectric transducers embedded in silicone rubber and inserted into the mid-sole of a shoe. These transducers are used to obtain force measurements for studies on the interaction between the foot and the shoe while walking. The device further includes a back pack containing amplification and multiplexing circuitry. Medical and Biological Engineering and Computing, Foot-Force Measuring Device for Clinical Assessment of Pathological Gait, Miyazaki, et al., July 1978, discloses a force transducer that is attachable to a shoe, in combination with an amplifier transmitter and a receiver processor unit for measuring the static and dynamic forces acting between the foot and the floor during walking. *The Complete Handbook of Athletic Footwear*, Cheskin, Melvyn P., Fairchild Publications, New York, 1987, P. 158, discloses a flashing safety light component for use with running shoes. The device is attachable, by cement, to the heels of running shoes and functions as a night-running safety device.

None of the foregoing references teach or suggest the invention claimed herein.

OBJECTS AND SUMMARY OF THE INVENTION

According to one aspect of the present invention, there is provided a product, preferably an athletic shoe or athletic apparel, adapted to emit light, sound energy or information in response to impact. The product comprises a molded part having a battery-powered light- or sound-emitting unit or a liquid crystal device at least partially molded therein. The unit comprises an impact-sensing element made from a polymeric piezoelectric material, a battery means, a light- or sound-emitting device or an information display device and a circuit connected to said piezoelectric material. The unit is responsive to electrical energy produced upon impact which permits the light or sound-emitting device to be energized from the battery or any information displaying device to be activated.

In one embodiment, the electrical energy resulting from each impact is used as a trigger to operate the light- or sound-emitting unit via the circuit incorporated therein, and the amount and/or duration of the light or sound emission can be independently determined/controlled by appropriate design of the circuit.

The circuit preferably comprises a monostable circuit such as a monostable multivibrator or the like, the time constant of which determines the duration of energization of the light- or sound-emitting device and may advantageously be adjustable, for example by means of a variable resistance.

Where the product includes a light-emitting device, the device may be a light-emitting diode ("LED") or a gas discharge lamp such as a neon lamp. Additionally, the light-emitting device may be disposed within the product, and the product may further include optical fiber means arranged to conduct light emitted by said light-emitting device to an outside surface of the product. Where the product contains an information display device, a liquid crystal device may be used.

The product is preferably a shoe, particularly a running shoe or a jogging shoe. The molded part is preferably a unitary sole-and-heel structure, with at least the battery, the circuit and the light-emitting device disposed in or molded into the heel part of the structure, and with the light-emitting device being arranged to emit light rearwardly from said heel part. The polymeric piezoelectric material may be molded into the sole part of the structure, preferably in the region of maximum stress.

Another embodiment of a shoe may include a plurality of light-emitting devices, either positioned at a plurality of points over the outside upper surface of the shoe or connected to said plurality of points via respective optical fibers. These light emitting devices are selectively energizable in a predetermined sequence, for example in response to successive groups or groupings of a predetermined number of impacts sensed by the impact-sensing element.

In still another embodiment, the circuit responds to the magnitude of the electrical energy produced by the piezoelectric material and thereby selectively energizes one or more of the light emitting devices depending on the amount of electrical energy produced. In this manner, a visual indication of the magnitude of the pressure exerted upon the sole of the shoe can be displayed.

In another embodiment, the light emitting devices may also be arranged to form a bar graph display. This embodiment is particularly suitable for use as an exercise shoe in performing sequences of different exercises, since different light-emitting devices, perhaps differently colored, can be energized for each different exercise.

According to another aspect of the invention, the shoe is provided with a plurality of light-emitting devices, and with temperature sensing means responsive to the temperature within the shoe in addition to or instead of the piezoelectric material. In this embodiment, the circuit, additionally or alternatively, responds to the temperature sensing means so as to selectively energize the light-emitting devices and provide a display indicative of the temperature within the shoe. Thus the light-emitting devices may be of different colors, a first color, for example green, representing a normal temperature, a second color, for example orange, representing a somewhat higher and/or lower temperature, and a third color, for example red, representing an even higher and/or lower temperature, the devices being arranged as a linear array.

In yet another embodiment, the circuit, additionally or alternatively, energizes at least one light-emitting device, independent of the piezoelectric material, at a preset or a programmable rate or rates so as to provide a pace-setting facility to the wearer of the shoe. Advantageously, the circuit also responds to the electrical energy produced by the piezoelectric material to modify the programmable rate or rates so as to tend to assist the wearer of the shoe to compensate for any difference in actual pace as compared to the initially programmed pace rate or rates.

Alternatively, a shoe with a plurality of light-emitting devices can also incorporate a plurality of impact-sensing elements distributed throughout the sole of the shoe; the circuit energizing the light-emitting devices in accordance with the relative stress sensed by each impact-sensing element so as to provide an indication of the weight distribution over the sole of the shoe or the suspension, compression, cushioning efficiency energy return and/or impact of the shoe on the surface. This embodiment is particularly suitable for use as an athletic, gymnastic or dancing training shoe, since it can provide useful information on the style or angle of foot-ground contact of an athlete, gymnast or dancer wearing it.

In another embodiment, a shoe containing one or more impact sensing elements which may be distributed throughout the sole of the shoe, a battery, information processing circuitry connected to the impact sensing element or elements responds to impact by displaying appropriate information on an information display device such as a liquid crystal display (LCD).

According to another aspect of the present invention, a shoe containing an impact-sensing element made from polymeric piezoelectric material, a battery, a light-emitting device, and a circuit connected to the impact-sensing element responds to impact by energizing the light-emitting device. An optical fiber means is arranged to conduct the light emitted by the light-emitting device to an outside surface of the shoe, preferably an upper surface (i.e. a surface visible when the sole of the shoe is flat on the ground).

Thus, the optical fiber means may comprise a single optical fiber at least a part of which runs around the outside upper surface of the shoe, said part having a plurality of notches therein so as to emit light at each notch. The notches may be colored, e.g. with different colored translucent inks or dyes, so that the emitted light is correspondingly colored.

Alternatively, the optical fiber means may comprise a bundle of optical fibers, each fiber conducting the emitted light to a different point in the outside upper surface of the shoe: for example, where the shoe has a tongue, at least some of the fibers may terminate in the free end of the tongue. These points may form an abstract or geometrical pattern of light, or a logo or one or more alphanumeric characters constituting, for example, a trademark of the manufacturer of the shoe. The ends of the fibers at these various points may be colored, e.g. with different colored translucent inks or dyes.

The product may also be a fishing lure, wherein optical fibers conduct the emitted light to different points of the outside surface of the lure.

The product may also be a ball, for example, wherein at least its radially outer region is molded in a translucent polymeric material, and includes two light-emitting devices both arranged to be simultaneously energized by the circuit, the light emitting devices being arranged to emit light in generally opposite directions.

BRIEF DESCRIPTION OF THE DRAWINGS

The invention will now be described, by references to the accompanying drawings, of which:

FIG. 1 shows a side view of one embodiment of the present invention wherein an athletic shoe incorporates a piezoelectric impact sensor;

FIG. 2 shows a cross-sectional view of another embodiment of the present invention wherein a ball incorporates a piezoelectric impact sensor;

FIG. 3 shows a schematic diagram which includes a monostable multivibrator circuit for incorporation into a product of the present invention, for example, the athletic shoe of FIG. 1;

FIG. 4 shows a top schematic view of an athletic shoe of the present invention wherein the light-emitting diode is mounted in the sole in front of one end of a light-transmitting optical fiber bundle and the other end of these fibers terminate at various points on the outside upper surface of the shoe;

FIG. 5 shows a top schematic view of an alternative embodiment of an athletic shoe of the present invention wherein the light-emitting diode is mounted in the sole in front of one end of a light transmitting optical fiber bundle;

FIG. 6 shows an enlarged view of an optical fiber of the athletic shoe of FIG. 5;

FIG. 7 shows a top schematic view of an alternative embodiment of the athletic shoe of the present invention wherein piezoelectric impact sensors are located in various locations in the sole and heel of the shoe;

FIG. 8 shows a top schematic view of an alternative embodiment of the athletic shoe of the present invention wherein a plurality of light emitting diodes are mounted in front of one end of an optical fiber bundle, and the fibers of the opposite end of the optical fiber bundle are embedded in various locations on the outside upper surface of the shoe;

FIG. 9 shows a schematic view of an embodiment of the present invention wherein the product is a fishing lure;

FIGS. 16 and 16A show a combination exploded view and phantom view of the shoe of FIG. 15 showing the location of the components of the present invention;

FIGS. 17 and 17A show a partial side plan view of the shoe of FIG. 15 showing the piezoelectric impact sensor over the cushioning pad in the heel section of the shoe;

FIGS. 18 and 18A show a partial exploding view of the electronics capsule comprising the circuit and battery for use in connection with an athletic shoe of the present invention;

FIG. 19 shows a cross-sectional view of the components comprising the electronics capsule shown in FIG. 18;

DETAILED DESCRIPTION OF THE INVENTION

Figure 10:
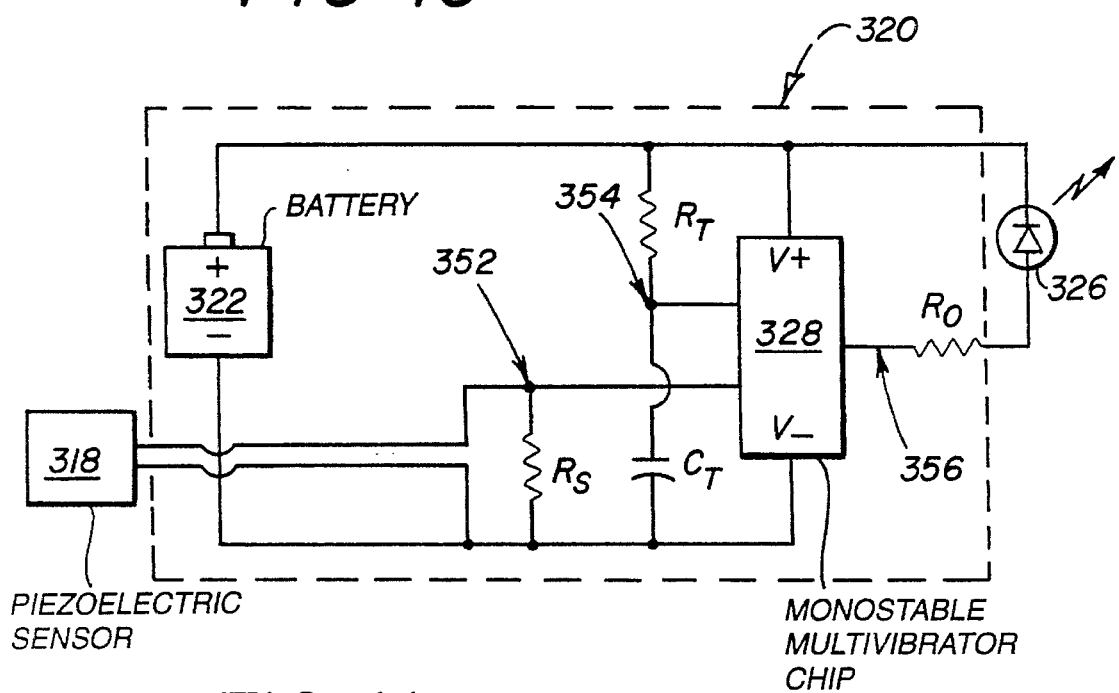
FIG. 10 shows a schematic which includes an alternate monostable multivibrator circuit for incorporation into the various embodiments of the present invention.

The shoe 210 shown in FIG. 1 comprises a unitary sole-and-heel structure 212 attached by molding or other means to an upper 214. The sole-and-heel structure 212 may be molded to the upper using methods well known in the art.

Located or molded within the sole 216 of the sole-and-heel structure 212, preferably adjacent to a point of maximum stress (i.e. near the part corresponding to the ball or heel of the wearer's foot) is a piezoelectric impact sensor 218 comprised of a sheet or layer of polymeric piezoelectric material. This piezoelectric impact sensor 218 preferably comprises polyvinylidene fluoride (PVDF) which has been stretch oriented and electrically polarized to enhance its piezoelectric properties. Such materials are known in the art. Referring to FIGS. 1 and 3, the piezoelectric impact sensor 218 is electrically connected to a circuit 220 which contains a battery pack 222, preferably a mercury, silver oxide or lithium battery, molded into the heel 224 of the sole-and-heel structure 212.

Referring to FIG. 3, the circuit 220 when triggered by the piezoelectric impact sensor 218, energizes a light-emitting diode (LED) 226. The LED 226 may be located or molded into the heel 224 so as to emit light rearwardly therefrom.

In use, as the wearer of the shoe 210 walks, runs, jogs or moves, the piezoelectric impact sensor 218 produces a pulse of electrical energy each time the sole 216 of the sole and heel structure 212 impacts the ground, i.e. at each step or stride of the wearer, by virtue of the piezoelectric effect. Each pulse of electrical energy triggers a monostable circuit 256 such as a multivibrator circuit or the like within the circuit 220.

Triggering the monostable circuit 256 allows the LED 226 to light for a time period determined by the resistor 258 and capacitor 260. Resistor 258 can be variable or a fixed and could be used to preselect the amount of time that LED 226 will be lit.

In use, a bright flash of light is emitted rearwardly from the heel of the shoe 210. Thus the wearer of a pair of the shoes 210 is clearly visible from behind by virtue of the flashes of light emitted rearwardly with each stride, which has considerable advantages from a safety point of view for runners and joggers on public roads, particularly in low light conditions.

In another embodiment, the circuitry can be molded or encapsulated with the battery or batteries and the LED. The piezoelectric impact sensor can then be attached to any surface of this encasement and then installed in a shoe such that the LED is visible from the rear of the shoe or from some point along the circumference of the sole. In an alternative version of this embodiment, the LED can be extended via wires to remote locations of the sole, heel or upper of the shoe while the encapsulated circuitry, battery, and impact sensor are located in an area of maximum impact. A plurality of these devices could be located throughout the shoe.

In yet another embodiment, of the shoe, the circuitry can be modified to operate other devices such as an electronic pedometer. In this embodiment, the circuitry reacts to impacts sensed by the piezoelectric impact sensor that exceed a certain magnitude or preset value, e.g., as when a wearer of the shoe is actually walking or running. The impacts that exceed this preset value are used to drive a digital display, thus counting the number of steps or strides taken.

FIG. 3 shows a schematic diagram for circuit 220. The circuit 220 comprises a pair of inputs 252 electrically connected to the piezoelectric impact sensor 218 and to the control input 254 of a monostable circuit 256. The monostable circuit 256 has a timing circuit comprising a resistor 258 (either variable or fixed) and a capacitor 260, electrical power supply inputs connected to the battery pack 222, and outputs 262 connected to the LED 226. Adjustment or selection of the value of the resistor 258 determines the duration of the time period for which the monostable circuit 256 allows the LED 226 to light in response to each impact sensed by the piezoelectric impact sensor 218.

FIG. 10 shows another monostable multivibrator circuit 320 that can be incorporated in the articles of this invention. In this embodiment, the stress of an impact, such as when the shoe strikes the ground, causes a piezoelectric impact sensor 318 to generate a voltage trigger or pulse. This trigger is applied across resistor $R_s$ and to the input 352 of the monostable multivibrator chip 328. Triggering the input causes the output of chip 328 to turn on LED 326 connected to the output 356 via a current limiting resistor $R_o$ and causes the capacitor $C_T$ to discharge. The value of resistor $R_o$ is selected to maximize the brightness of LED 326.

After the output of chip 328 is triggered to turn on the LED 326, capacitor $C_T$ begins to charge through resistor $R_T$. When the voltage across capacitor $C_T$ at input 354 reaches, for example, about two-thirds of the value of the battery voltage, the chip 328 is reset and the LED 326 is turned off. The amount of time that it takes for capacitor $C_T$ to charge to two-thirds of the battery voltage is determined by the R-C time constant selected by the values used for the resistor $R_T$ and capacitor $C_T$.

After the chip 328 is reset, it returns to a quiescent state. In the quiescent state, capacitor $C_T$ completely charges to the value of the battery voltage and a minimum of current flows through the LED 326. The circuit in this quiescent state thus maintains a minimum current draw so as to achieve maximum battery life.

The value selected for resistor $R_S$ controls the sensitivity of the piezoelectric impact sensor 318. Different values vary the amount of loading and thus control the magnitude of the trigger voltage applied to the chip 328. The value selected for resistor $R_O$ controls the current flow through LED 326. This resistor value will depend on the voltage of battery 322 and the amount of current required to achieve optimum brightness of LED 326.

Figure 11:
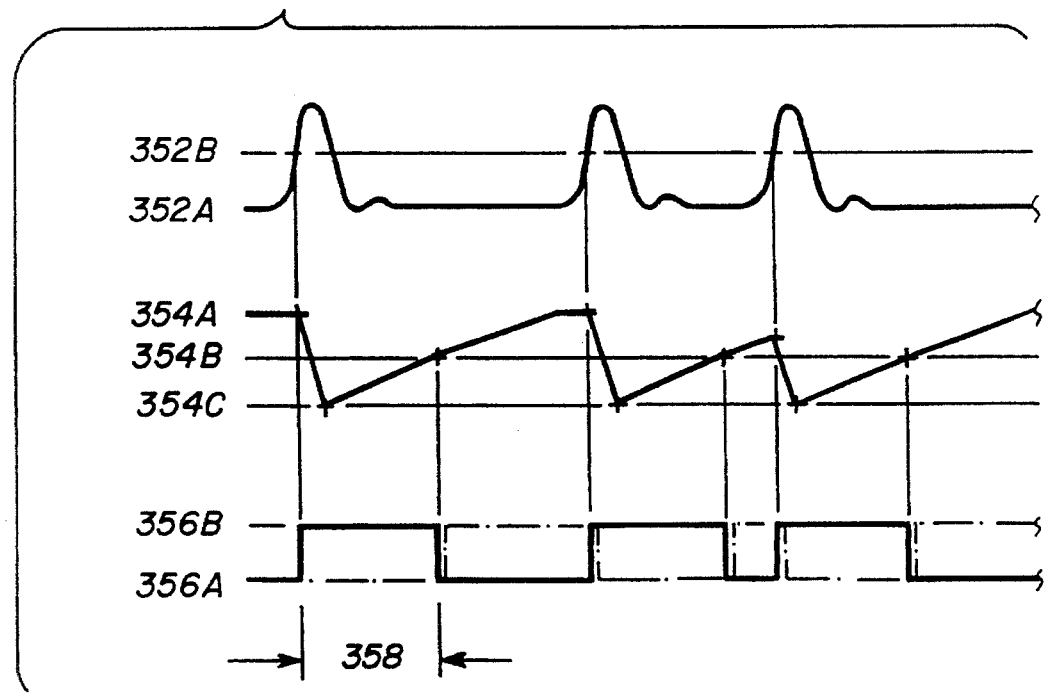
FIG. 11 is a graphical representation of the signal output of the circuit of FIG. 10 showing the response to impacts caused by walking or running.

FIG. 11 shows a graphical representation of the waveforms generated by the circuitry of FIG. 10 and the on/off times of LED 326. In the quiescent state, i.e., no impacts, the voltage applied to input 352 of chip 328 is at a minimum level 352A. When the piezoelectric impact sensor 318 senses an impact or similar stress, it generates a voltage peak. When this peak- exceeds a preselected level 352B, as determined by the selection of an appropriate value for resistor $R_S$, then the input 352 of chip 328 is triggered and the monostable multivibrator changes state.

In the quiescent state, capacitor $C_T$ is charged to the voltage of battery 322. Thus, at this time, the input 354 is held "high" as shown by the quiescent input 354A of FIG. 11. Triggering the chip 328 causes capacitor $C_T$ to rapidly discharge to the input "low" level 345C. At this point, capacitor $C_T$ starts to charge through timing resistor $R_T$. When the voltage across capacitor $C_T$ reaches, for example about two-thirds of the battery voltage, then this input "high" voltage 354B resets chip 328 and turns off the LED 326.

Thus, when an input signal from the piezoelectric impact sensor 318 exceeds the trigger input level 352B, chip 328 turns LED 326 on by outputting an output "low" level 356B. After capacitor $C_T$ recharges to the reset input "high" level 354B, chip 328 turns LED 326 off by outputting an output high level 356A.

Figure 12:
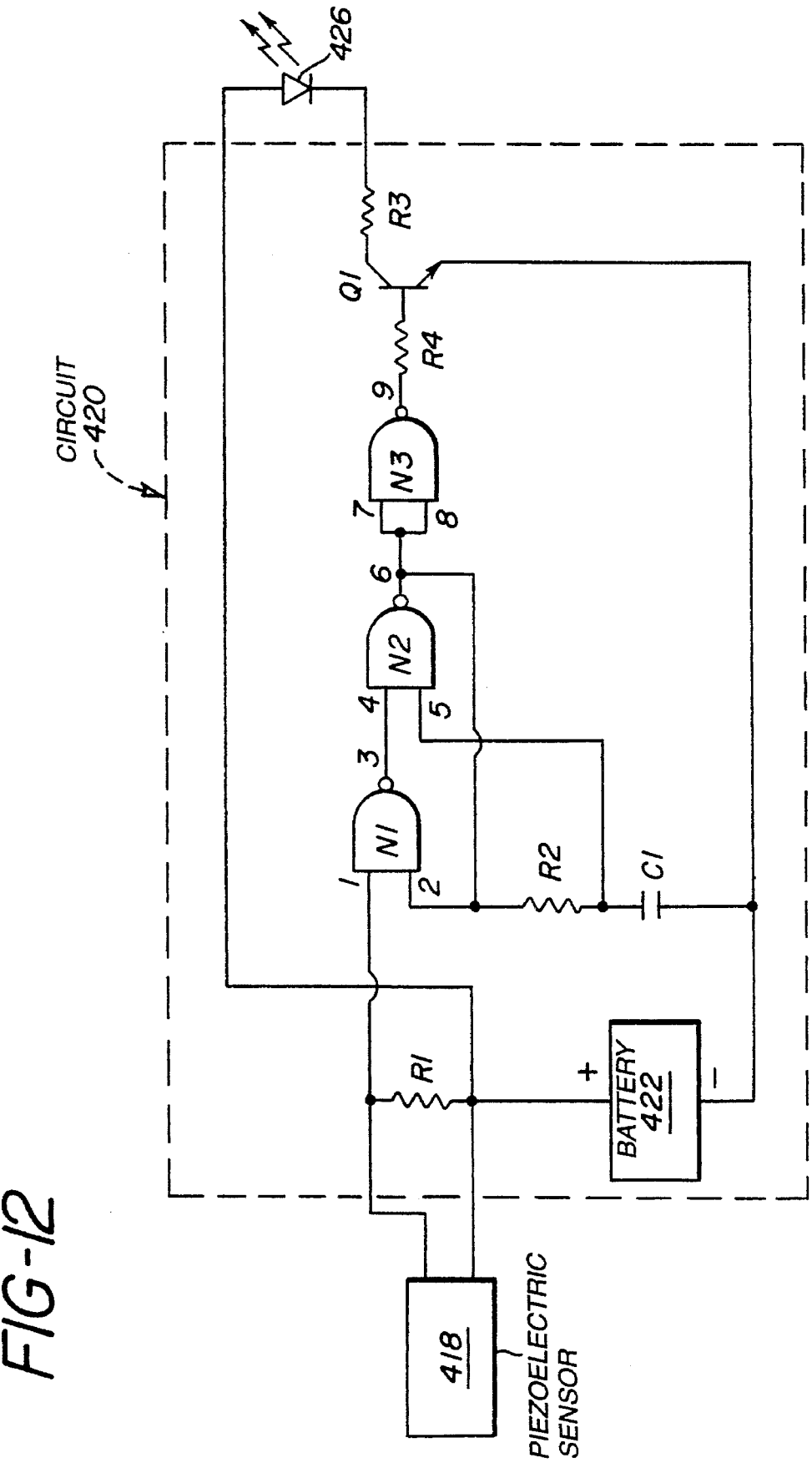
FIG. 12 shows a schematic of another embodiment of a monostable multivibrator circuit for incorporation in a product of the present invention.

FIG. 12 shows another circuit embodiment wherein a R-S (reset-set) latch circuit 420 can be incorporated in, for example, a shoe. This embodiment has the advantages of lower cost, minimum size and very low power consumption so as to offer extended battery life. In this embodiment, an impact on the piezoelectric sensor 418 is used to trigger a R-S latch which turns on an LED 426 for a time determined by a R-C time constant.

When an impact is felt by the piezoelectric impact sensor 418 shown in FIG. 12, such as when the shoe strikes the ground, the sensor 418 generates a small amount of current which passes through sensitivity resistor R1 and causes a decrease in the voltage or signal applied at point 1 of the R-S latch-comprising NAND gates N1 and N2.

Selection of various values of sensitivity resistor R1 is used to adjust the sensitivity of the circuit 420. Using a lower value of resistance for R1 requires a larger current flow through resistor R1 to produce a signal large enough to trigger the R-S latch; thus, decreasing the sensitivity of the circuit 420 to signals generated by the impact sensor 418. Likewise, a higher value of resistance used for R1, increases the sensitivity since a larger signal is produced for a given current generated by the impact sensor 418.

Thus, when the impact sensor 418 senses an impact, the signal it generates causes the input voltage applied to point 1 of NAND gate N1 of the R-S latch to go low. The output of NAND gate N1 then goes high which causes the output of NAND gate N2 of the R-S latch to go low.

The low output of NAND gate N2 causes the invertor N3 output to go high and turn on transistor switch Q1. Turning on transistor switch Q1 allows current to flow through the collector branch of this transistor and thus turn on LED 426. Thus, an impact sensed by the piezoelectric sensor 418 causes the R-S latch to set and via transistor Q1 to turn on LED 426.

The value of the LED current limiting resistor R3 is determined by the current required to produce the optimum brightness level of LED 426. Thus, the resistor R3 value depends on the current required, the battery voltage, and the LED 426 and transistor Q1 voltage drop when this current is flowing through the collector circuit of transistor switch Q1.

Referring to FIG. 12, a bias resistor R4 can be inserted in the base-emitter circuit of transistor switch Q1 to limit the base-emitter current and thus conserve battery life. In another embodiment, resistor R4 can be omitted in order to conserve space but at the cost of reduced battery life. For example, if the LED 426 draws 20 to 25 mA of current and the base-emitter circuit of transistor switch Q1 draws 2 to 2.5 mA of current without a bias resistor, then the battery life can be expected to be shortened by about ten percent due to the increased current drain when transistor switch Q1 is turned on.

In addition to causing the LED 426 to turn on when the output of NAND gate N2 of the R-S latch goes low, the low output is simultaneously applied to the R-C timing circuit comprised of resistor R2 and capacitor C1. This low output causes capacitor C1 of R-C timing circuit (which had previously charged to the battery voltage) to discharge through timing resistor R2 and NAND gate N2. When the charge on capacitor C1 decreases, for example, to about one-half the value of the battery voltage; this low input signal is applied to point 5 of NAND gate N2, and causes the output of NAND gate N2 to go high again; thus resetting the R-S latch, turning off transistor switch Q1 and turning off LED 426 and allowing the R-C timing circuit to recharge to the battery voltage through NAND gate N2. In one embodiment, circuit 420 uses CMOS technology whose input threshold is about one half the power supply voltage. The use of CMOS technology provides an ideal match between the natural trigger threshold of NAND gate N2 and the trigger input generated by the discharge of capsulator C1 of the R-C timing circuit. In addition, the use of low-power CMOS devices extends battery life.

Resetting the R-S latch returns circuit 420 to a quiescent state and enables NAND gate N1 of the R-S latch to again respond to an impact trigger signal from the piezoelectric impact sensor 418. The amount of time that the R-S latch holds the LED 426 on is determined by the R-C timing circuit of resistor R2 and capacitor C1. By varying the value of either of these components, the amount of time the R-S latch holds the LED 426 on can be increased or decreased.

While the R-S latch is set, i.e. the R-S latch is holding LED 426 on, all signals generated by impact sensor 418 are ignored by the NAND gate N1 of the R-S latch.

Figure 13:
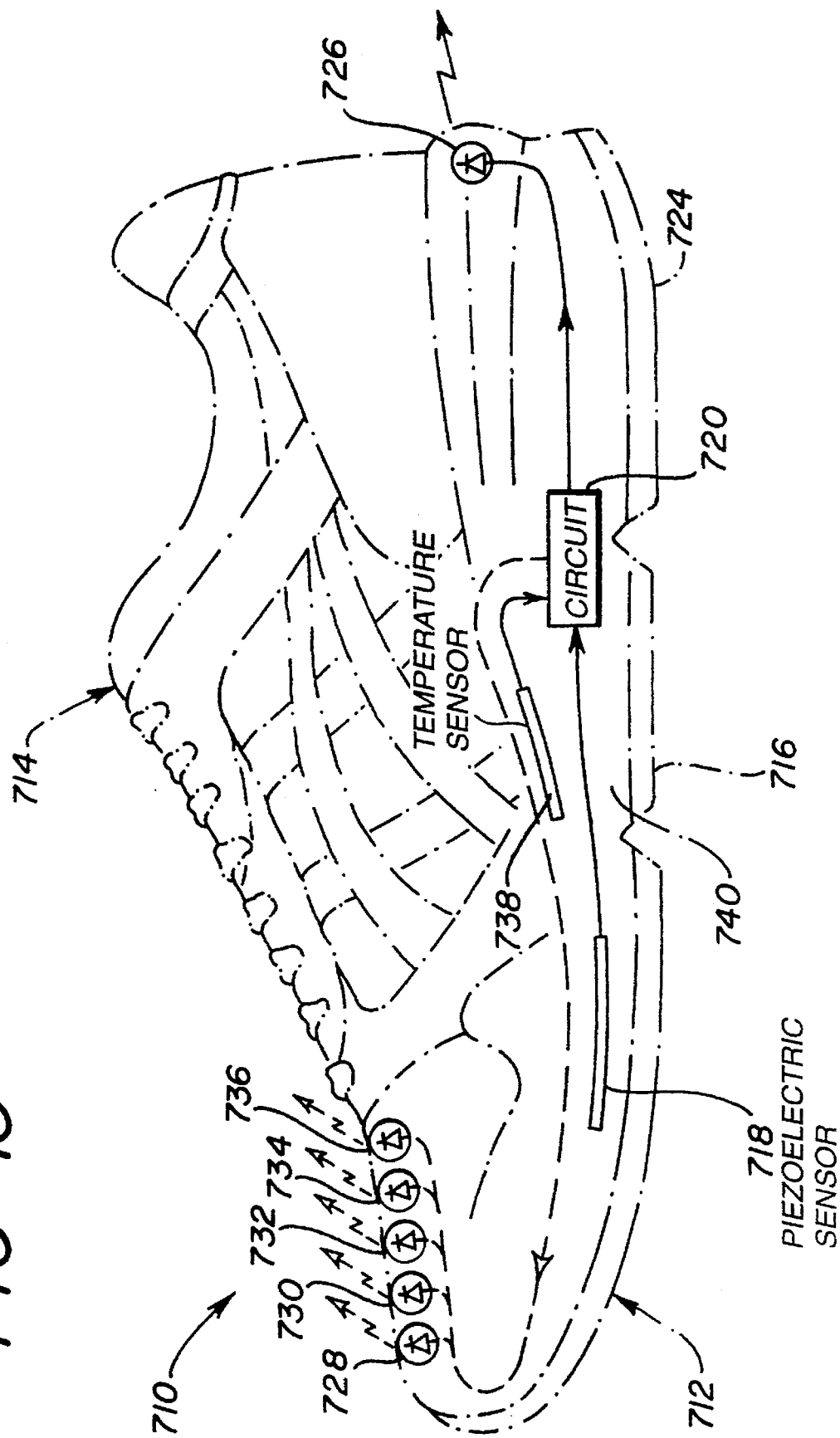
FIG. 13 shows another embodiment of an athletic shoe of the present invention wherein a plurality of light-emitting diodes are positioned on the shoe.

FIG. 13 depicts another embodiment of a shoe of the present invention incorporating the circuitry described herein. The shoe 710 of this embodiment is provided with numerous light emitting devices such as LEDs 728 through 736, one or more impact sensors 718, a temperature sensor 738 and an appropriate circuit 720 to process the impact and the temperature information. In this shoe, FIG. 14, a circuit such as circuit 720 may be used to process impact information and use this information to turn on light emitting devices such as LEDs 728 through 736 so as to display a bar graph, or to use the magnitude of the impact to light or flash individual LEDs.

It is also within the scope of this and the other embodiments of this invention to use a circuitry responsive to temperature, which can process such temperature information so as to display temperature graphically via LEDs.

Referring to FIG. 13, the shoe 710 incorporates within the sole and heel structure 712, a piezoelectric impact sensor 718, a temperature sensor 738 and a circuit 720 to process the signals received from these sensors. LEDs 728 through 736 are incorporated in the vicinity of the toe portion of the upper 714 section of the shoe 710. These LEDs are typically positioned so as to be visible to the wearer while walking or running. Likewise, an LED 726 may be mounted in the heel 724 of the shoe 710, and facing rearward so as to be visible to vehicles or individuals approaching from the rear.

Figure 14:
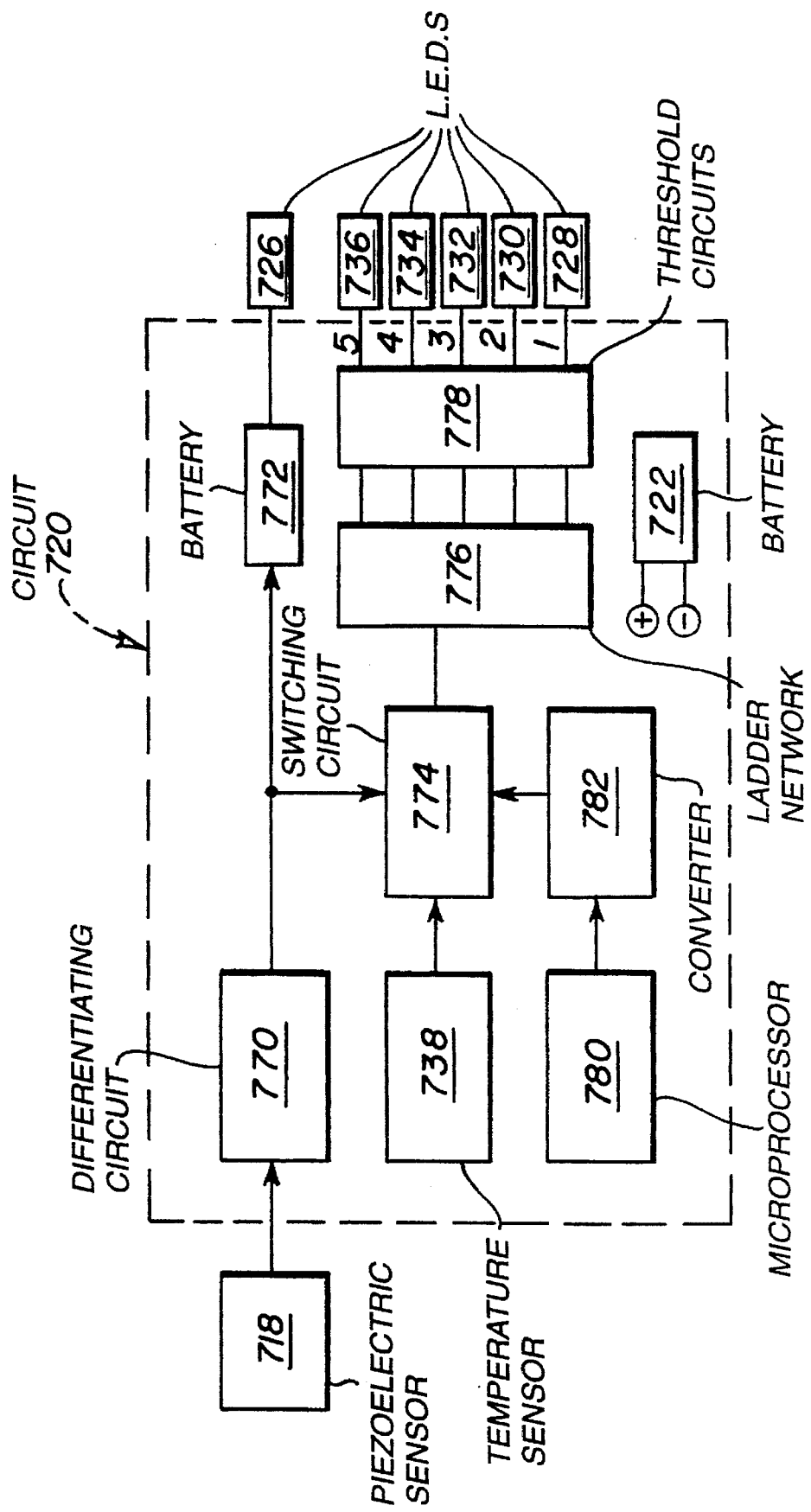
FIG. 14 shows a schematic for another circuit for use in connection with a product of the present invention.

Referring to FIG. 14, circuit 720 of FIG. 14 illustrates a functional circuitry that may be used to process the information generated by the sensors 718 and 738 of the shoe 710 of FIG. 13 and to control the LEDs 726 through 736 incorporated in shoe 710. Referring to FIG. 14 a microprocessor 780 can be included in circuit 720, to provide preprogrammed control of the LEDs 728 to 736 and/or to evaluate the input from an impact sensor 718 and/or a temperature sensor 738 and then light appropriate light emitting devices (718 to 736). Also, a means of generating audible sounds (not shown) could be substituted for or included in addition to the light emitting devices.

Circuit 720 can process the input signals from either:

(1) the piezoelectric impact sensor 718 to light various LEDs, such as LED 726, and optically LEDs 728 through 736, to indicate the magnitude of the impacts suffered by the shoe; or (2) the temperature sensor 738 to light various LEDs, such as LED's 728 through 736, to indicate various temperature levels within the shoe.

The circuit 720 of FIG. 14 is powered by a battery pack 722. Circuit 720 comprises an input from piezoelectric impact sensor 718 which is applied to differentiating circuit 770 and a three state switching circuit 774 which selects one of three inputs to drive a ladder network 776. The ladder network 776 has five outputs, each corresponding to a higher output voltage. Each of these outputs are connected via threshold circuits 778 to the appropriate LED, e.g. 1st LED, 728; 2nd LED, 730; 3rd LED, 732; 4th LED, 734; and 5th LED, 736.

Assuming the switching circuit 774 is set to couple the output of the differentiating circuit 770 to the ladder network 776, then the greater the impact pressure on the piezoelectric impact sensor 718, the greater the voltage at the output of the differentiating circuit 770. This greater voltage increases the number of active outputs of the ladder network 776 which in turn, causes the threshold circuit 778 to turn on the appropriate number of the LEDs 728, 730, 732, 734 or 736. Thus, by lighting from one to five of these LEDs, a bar graph display of impact pressure can be seen on the toe portion of the upper 714 section of shoe 710 (see FIG. 13).

The switching circuit 774 can also be set to connect the temperature sensor 738 to the input of the ladder network 776. In this case, the LEDs 728, 730, 732, 734 and 736 provide the wearer of the shoe 710 a bar graph display of the temperature adjacent the instep region of the sole 716 (see FIG. 13). The temperature sensor 738 may be a National Semiconductor type LM35 temperature sensor, a thermistor, a temperature sensing diode, or the like, together with an amplifier where necessary. The temperature sensor can be mounted in various other locations within the shoe structure to provide a bar graph display of the temperature of the adjacent region.

As an alternative to a bar graph display of temperature, the LEDs can be of different colors, e.g., LED 728, red; LED 730, orange; LED 732 green; LED 734 orange; and LED 636 red, or the like, with green lit to indicate normal temperature, orange lit to indicate a higher and/or lower than normal temperature, and red lit to indicate a much higher and/or lower temperature.

The switching circuit 774 can also be set to connect the output of a programmable microprocessor 780 via a digital to analog (D/A) converter 782 to the ladder network 776. The microprocessor 780 is preprogrammed, such as by a plug-in or a masked ROM (read-only memory) or PROM (programmable read only memory) means (not shown) or the like, to produce a series of digital pulses which are converted via the D/A converter 782 into an analog trigger signal and applied to the ladder network 776 via the switching circuit 774. The microprocessor 780 controls the amplitude and frequency of the signal produced by the D/A converter 782. Thus, the microprocessor 780 can cause one or more of the LEDs 728, 730, 732, 734, and 736 to light/flash at a rate chosen to set a desired pace or series of paces (a pacing mode) for a given distance to be walked, run or raced.

The switching circuit 774 can be manually switched between its three inputs by a manually operative switch means (not shown), or it can automatically cycle between two or all three of the various inputs, e.g. impact, temperature and pacing.

Many modifications can be made to the described embodiments of the invention. For example, in the "pacing mode" additional circuit means can be added so that the microprocessor can sense the actual pace by using the impacts sensed by the piezoelectric impact sensor. The microprocessor can then adjust the pattern displayed by the LEDs to try to compensate for any shortfall or excess between the initial set pace and the actual pace. In a further embodiment, the switching circuit 774 can cycle between the microprocessor 780 for a pace setting display and the temperature sensor 738 to provide a visual warning in the event the temperature sensed within the shoe 710 becomes excessively high.

In an alternative embodiment (not shown) similar to the embodiment of FIGS. 13 and 14, the shoe is provided with one or more input sensors, such as one or more piezoelectric impact sensors, and/or a temperature sensor, interface circuitry to connect these sensors to a microprocessor, a microprocessor to process the information and to then, via output control circuitry, to control various output devices; information display devices such as an LCD, light emitting devices such as one or more LED's or sound emitting devices. In addition to processing information from the input sensors, the microprocessor can provide preprogrammed control of the various output devices.

Many additional modifications can be made to the described embodiments of the invention. For example, FIG. 5 shows an athletic shoe of the present invention comprising a piezoelectric impact sensor 418, a R-S latch circuit 420, such as any of the circuits described herein, or the like, including a battery and an LED 426 which can be formed as a single encapsulated unit which is removably fitted into the heel 424 of the shoe. The LED 426 of this encapsulated unit is arranged to emit light rearward by transmitting the light emitted by the LED 426 via optical fibers 476 to points on the outside surface 474 of the heel 424.

Still referring to FIG. 5, an optical fiber 476 or other light guiding medium (e.g. a layer of suitable translucent plastic material) can be molded into the shoe 410, so as to guide the light emitted by the LED 426 to various external surfaces of the shoe, e.g. to an exit point 474 facing rearwardly from the heel 424, to one or more ribs 472, extending vertically up and down the heel or to loop around the front portion of the upper 414. This embodiment provides for ready replacement of the capsule when the battery is exhausted, or when an LED of one color is to be replaced with an LED of another color. Alternatively, just the battery can be arranged to be replaceable.

Optionally, as shown in FIGS. 5 and 6, at least a part of the optical fiber bundle can be replaced by a single optical fiber 476 which runs around the upper part 414 of the front of the shoe and which has a plurality of notches 478, distributed along its length. From each of the notches 478 light from the LED 426 is emitted. These notches 478, as well as the points 474 on the outside surface of the shoe can be colored, for example with different colored translucent inks or dyes, to create a variety of multi-colored effects.

Referring to FIG. 4, another embodiment of shoe 310 has a LED 326 used in conjunction with an optical fiber bundle 370, the individual fibers 372 can be arranged to conduct the light from the LED 326 to respective points 374 on the outside surface of the shoe, e.g. distributed in an abstract or a geometric pattern over the upper part of the front of the shoe, or distributed to form a logo or one or more alphanumeric characters constituting a trademark of the manufacturer of the shoe, or disposed throughout the free end of the tongue of the shoe.

Still referring to FIG. 4, the piezoelectric impact sensor 318 can be mounted in the heel or other impact sensitive area. Circuit 320 comprises a monostable multivibrator circuit, or the like, and a battery. Signals from impact sensor 318 trigger circuit 320 which then turns on LED 326 for a period of time determined by a resistor-capacitor time constant incorporated into circuit 320.

Referring to FIG. 8, in another embodiment, shoe 610 includes a plurality of light emitting devices disposed within the shoe. The light emitted by LEDs 680 are transmitted to a plurality of points 684 on the outside surface of the shoe via optical fibers 682. In this embodiment, piezoelectric impact sensor 618 triggers circuit 620. Circuit 620 then turns on all LEDs 680 or alternatively, circuit 620 could be designed to selectively light or flash various LEDs 680 in a sequential, random or other pattern.

A modification to this embodiment is to incorporate circuitry such as counter and gating circuits wherein successive impacts detected by the piezoelectric impact sensor are counted. Based upon these counts, the circuitry sequentially lights successive LEDs at different locations in the shoe. For example, on the occurrence of a certain number of counts, the circuitry could light a selected LED so as to cause it to flash say ten or twenty times. Upon the occurrence of the next preselected count value, the circuitry could successively, randomly or in some preselected order, cause one or more of the other LEDs to light and/or flash for a period of time or for a set number of flashes.

This modification is particularly useful in an exercise shoe, since the pattern of lights can be used to assist and/or indicate the timing of a sequence of different exercises, with perhaps a different color LED being selected for the various exercises.

A further modification of this embodiment is to incorporate microprocessors or counting circuitry to analyze and process the signal generated by impacts detected by the piezoelectric impact sensor and then to display a count or other information based upon this information processing on an information display device such as an LCD connected to the microprocessor or counting output circuitry.

Referring to FIG. 7, depicting still another embodiment of the present invention, in addition to a plurality of LEDs, shoe 510 may also incorporate a plurality of individual piezoelectric impact sensors 518A through 518D distributed throughout the sole 516 of shoe 510. In this embodiment, a circuit 520 is designed to light one or more LEDs 580 through 586 to reflect the relative stress sensed by the piezoelectric impact sensors 518 so as to provide an indication of the weight distribution over the sole of the shoe. This forms an excellent training aid for athletics, particularly runners, as well as for gymnasts and dancers, and is very effective if the athlete, gymnast or dancer is filmed in action with a video camera and the film is then played back in slow motion.

In embodiments of the shoe involving optical fiber bundles, one or more of the LEDs can, if desired, be omitted, their effect being achieved by use of ambient light. Thus, the optical fiber bundles act as light gatherers, so that if a bundle of their "input" ends is disposed, for example, all over the front of the shoe facing generally forwardly and upwardly, while their corresponding "output" ends are disposed in the heel, facing rearwardly and distributed to form, for example, a logo or alphanumeric character constituting a trademark, ambient light will in many circumstances be sufficient to make the "output" ends of the optical fibers appear to light up. Again, multicolored effects can be created, if desired, as described earlier.

Figure 15:
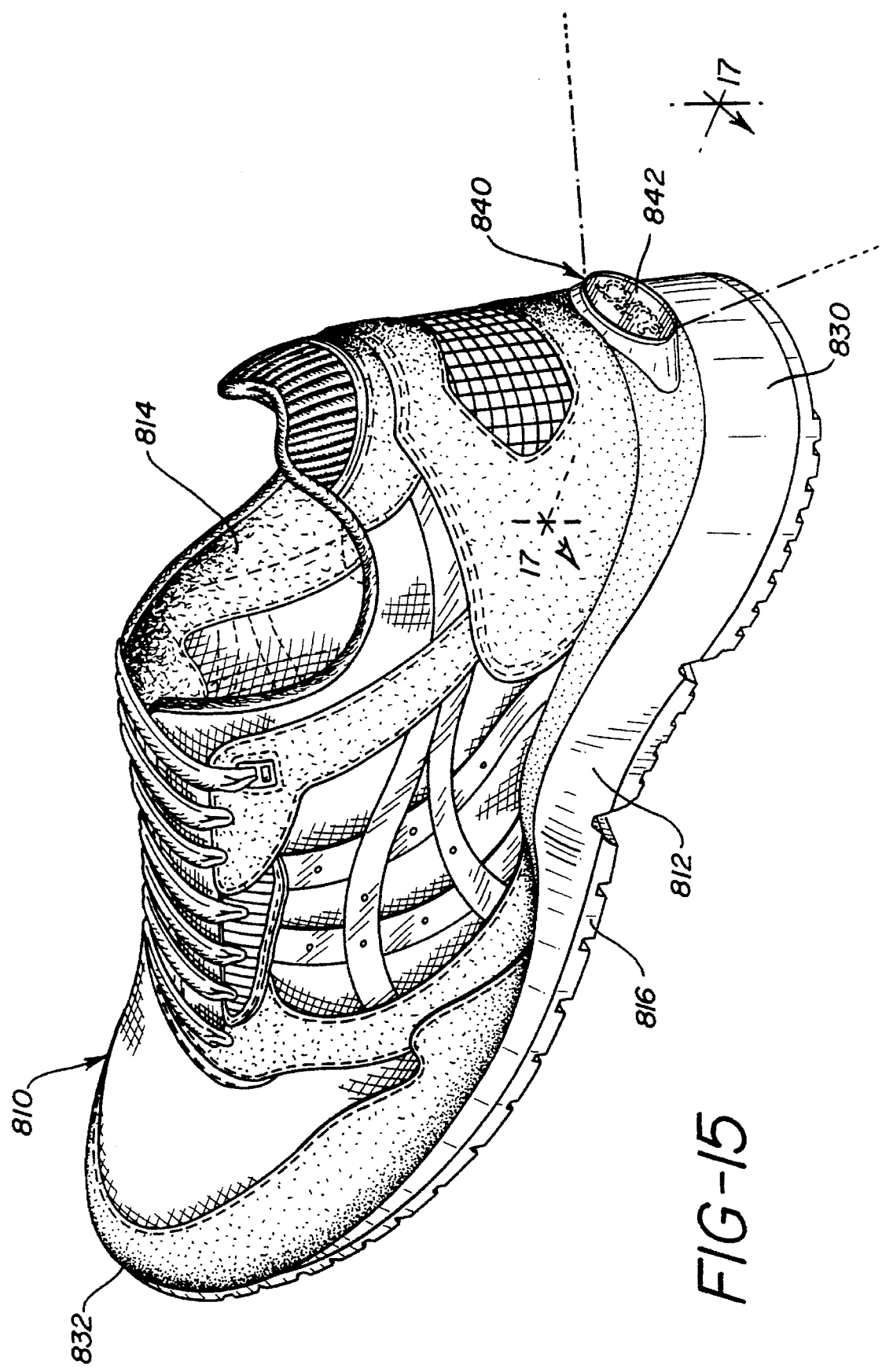
FIG. 15 shows a perspective view of another shoe of the present invention.

FIGS. 15 through 24 depict preferred embodiments of the shoe of this invention. Referring to FIG. 15, shoe 810 has a light unit 840 incorporated into the proximal end 830 of the shoe 810. The shoe 810 comprises a sole 816, a midsole 812, an upper 814, a proximal (or heel) end 830, a distal (or toe) end 832 and a light unit 840.

Figure 22:
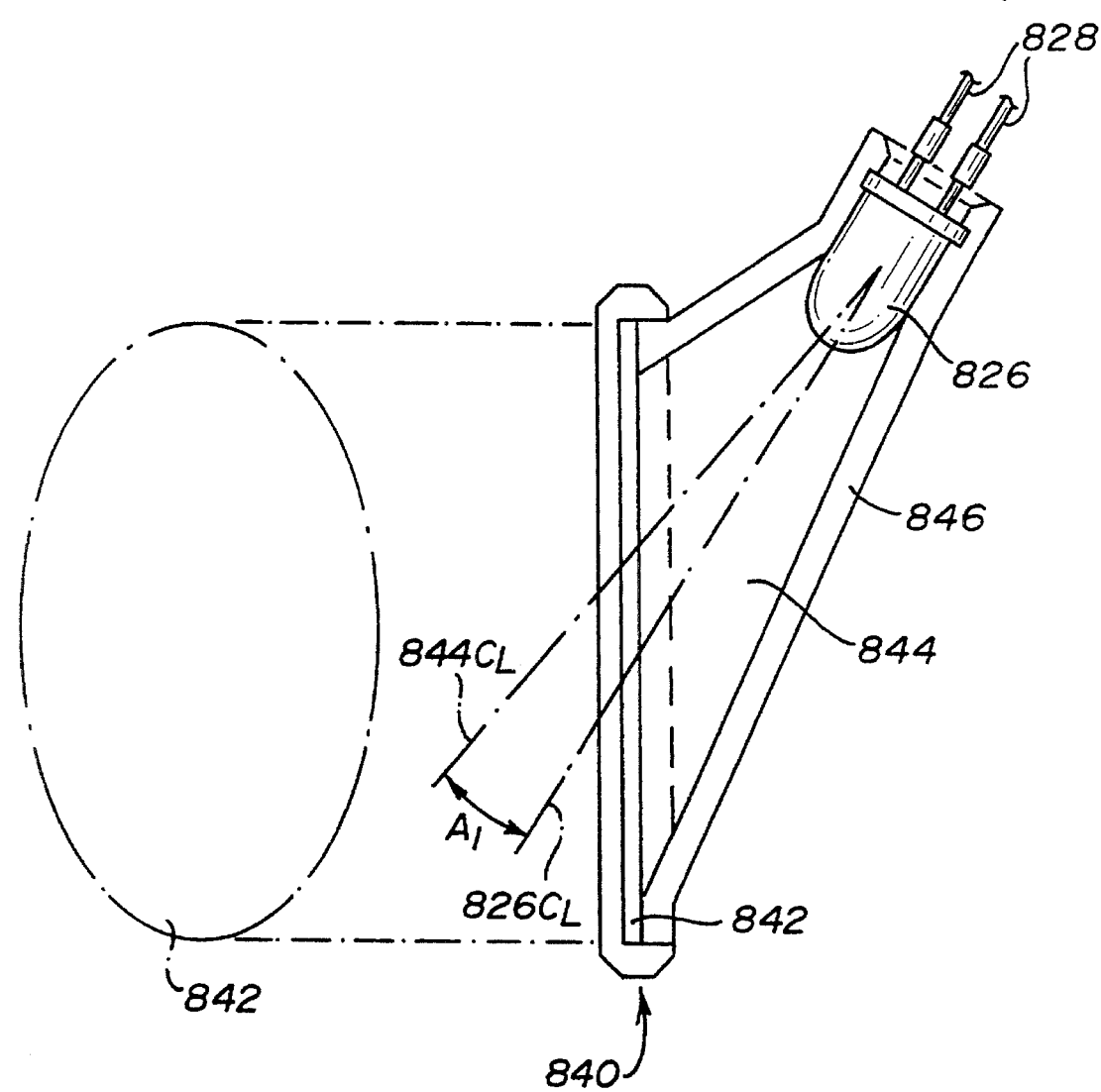
FIG. 22 is a diagram of the critical angles involved with positioning the light emitting diode in the heel of a shoe of the present invention.

The light unit 840 comprises a lens 842 on which a name or logo may be imprinted. When an internally mounted light emitting unit such as LED 826 shown in FIG. 22, is turned on, the logo or imprint is illuminated and is visible from the rear of the shoe.

The lens 842 can comprise translucent or colored material or a filter material so that the lens and/or imprint can be illuminated in various colors and/or textures to both improve the visibility of the shoe as viewed from the rear and to enhance the projection of any imprint thereon.

Positioning of components within this preferred shoe can be accomplished in any suitable manner. Referring to FIGS. 15 and 16, a piezoelectric impact sensor 818 is located in the proximal end 830 of the heel and covered by the heel cushion or liner 834. The sensor 818 is electrically connected to an electronics capsule 850 located in the midsole 812. The electronics capsule 850 may be mounted in any orientation in addition to the orientation shown. This electronics capsule contains the circuitry and battery pack required to process the signal generated by impacts on sensor 818. When a signal is generated by sensor 818 of sufficient magnitude to be detected by the circuitry of the capsule 850, this circuitry turns on LED 826 which is electrically connected to the capsule 850 via leads 828.

Figure 16A:
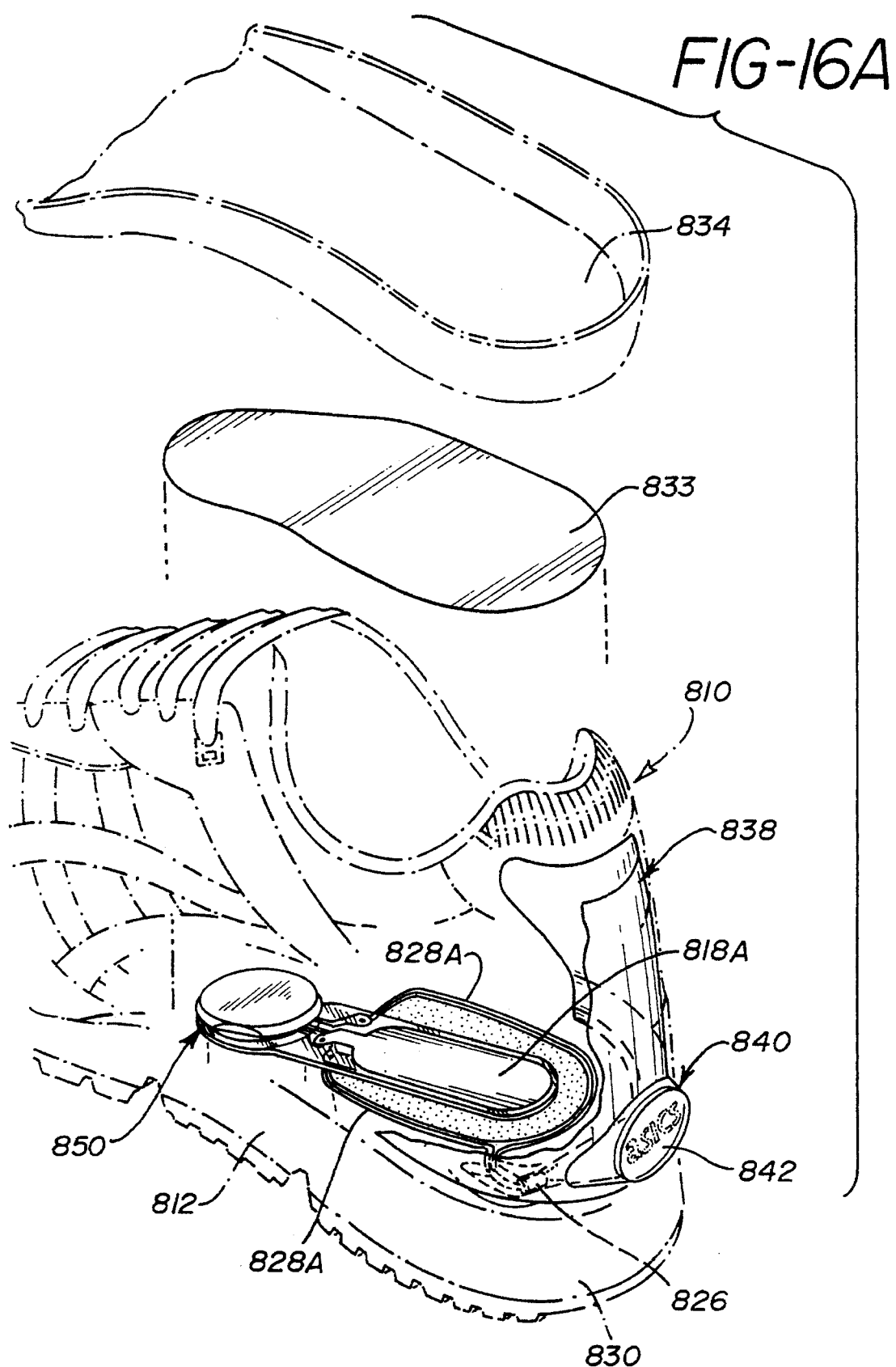

Referring to FIG. 16A, a piezoelectric impact sensor 818A is located in the proximal end 830 of the heel. This impact sensor 818A is covered first by a patch 833 which is subsequently covered by the heel portion or liner 834. The sensor 818A is electrically connected to an electronic capsule 850 located in the midsole 812. The electronics capsule 850 may be mounted in any orientation in addition to the orientation shown. This electronics capsule contains the circuitry and battery pack required to process the signal generated by impacts on sensor 818A. When a signal is generated by sensor 818A of a sufficient magnitude to be detected by the circuitry of the capsule 850, this circuitry turns on LED 826 which is electrically connected to the capsule 850 via leads 828A. The electronic capsule 850 may be insert molded to include the battery, circuit board and electronic components to provide mechanical and environmental integrity to the capsule 850.

Referring to FIG. 17, the piezoelectric impact sensor 818 may be located over a cushioning pad 836, for example, an encapsulated silicon gel cushioning pad, in the heel 838. This cushioning pad may include a plurality of partitions for directing the semi-liquid from one portion of the cushion to another.

Still referring to FIG. 17, locating the piezoelectric impact sensor 818 over the cushioning pad 836 enhances the magnitude of the signal generated by sensor 818. In this embodiment, when an impact force is applied to the impact sensor 818 as indicated by the downward arrow, the impact sensor 818 is further distorted as the cushioning pad 836 gives way beneath it. Since the magnitude of the signal generated by the piezoelectric impact sensor 818 is directly related to the amount of distortion applied to this sensor, the "give" of the cushioning pad permits the sensor 818 to have a greater distortion under the same force than it would if the sensor 818 had been mounted on a more rigid surface. Thus, for the same force, since the distortion with the cushioning pad present is greater, the signal generated by the sensor 818 will be greater.

Figure 17A:
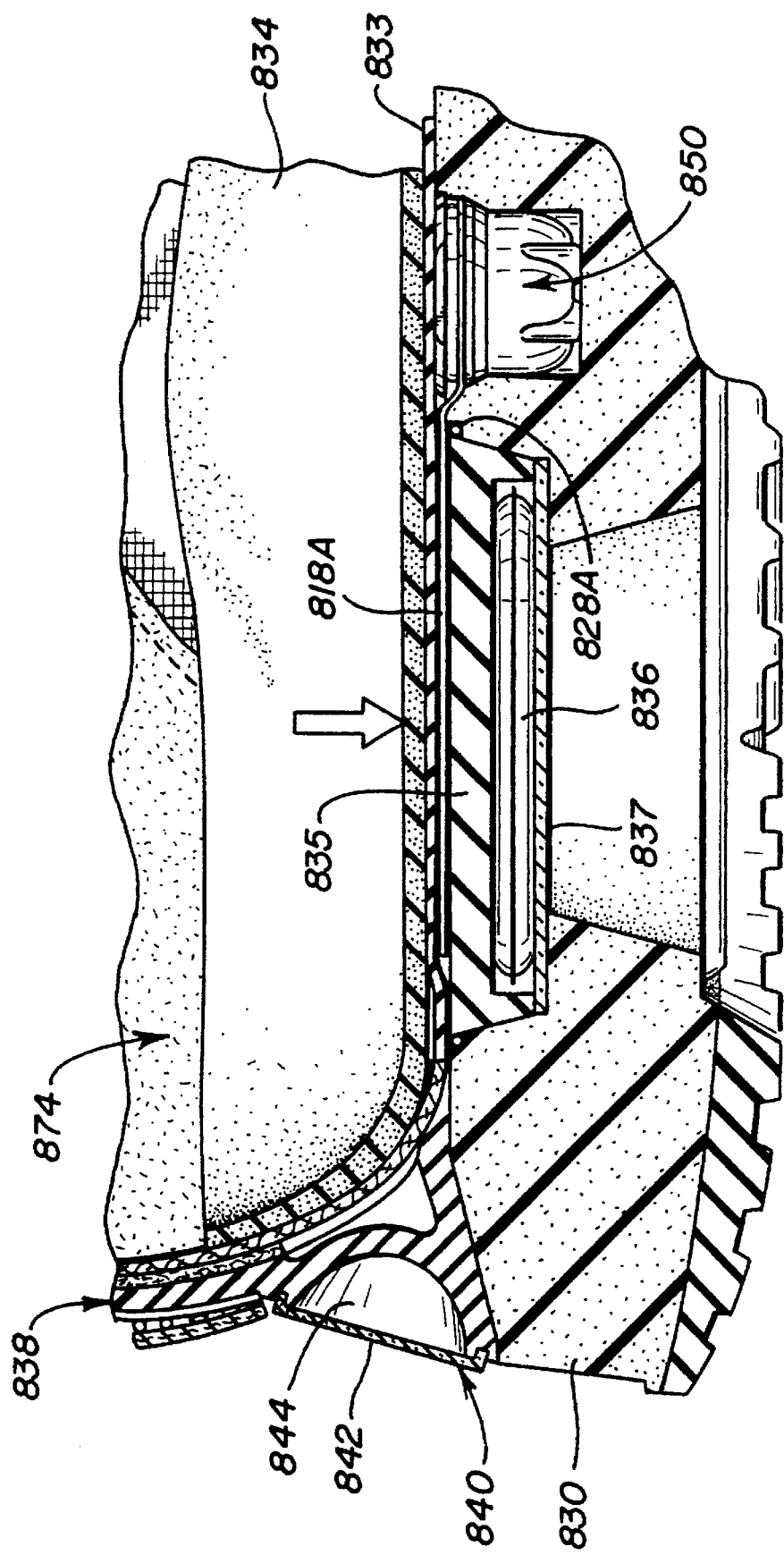

FIG. 17A illustrates another embodiment wherein the piezoelectric impact sensor 818A is located over the cushioning pad 836 in order to enhance the magnitude of the signal generated by sensor 818A. When an impact force is applied to the impact sensor 818A as indicated by the downward arrow, the impact sensor 818A is further distorted as the cushioning pad 836 gives way beneath it. Since the magnitude of the signal generated by the piezoelectric impact sensor 836A is directly related to the amount of distortion applied to the sensor, the "give" of the cushioning pad permits the sensor 818A to have a greater distortion under the same force then it would if the sensor 818A had been mounted on a more rigid surface. Thus, for the same force, since the distortion with the cushioning pad present is greater, the signal generated by the sensor 818A will be greater. The signal generated by sensor 818A is transmitted via leads 828A to the electronics capsule 850. In FIG. 17A, the electronics capsule is shown with its base mounted flush with the upper surface of the sole 816. This base and the associated impact sensor 818A is covered by patch 833. Patch 833 is subsequently covered by heel portion 834.

Still referring to FIG. 17A, the piezoelectric impact sensor 818A is located over the cushioning pad 836 which may be an encapsulated silicone gel cushioning pad positioned in the heel 838. This cushioning pad may include a plurality of partitions for directing the semiliquid from one portion of the cushion to another. This cushioning pad is typically covered with a GEL cap 835. A window 837 structure is typically located beneath the gel shock absorber 836.

FIG. 18 is a partial exploded view of a preferred embodiment of the present invention showing the electronics capsule 850, the piezoelectric impact sensor 818 and the LED leads 828 as used in shoe 810 of FIG. 16. The electronics capsule 850 may be mounted in any orientation in addition to the orientation shown. In this embodiment, a sheet of piezoelectric film is joined to a non-conductive flexible sheet 860. Conductive leads are deposited on this flexible sheet 860 and electrically connect the signal output from sensor 818 to circuit board 864. Conductive leads are also deposited on the flexible sheet 860 to electrically connect the outputs from circuit board 864 to LED leads 828. The conductive leads could also be printed on the flexible sheet (not shown).

FIG. 18A is a partial exploded view of another preferred embodiment of the present invention showing the electronics capsule 850, the piezoelectric impact sensor 818A and the LED leads 828A as used in shoe 810 of FIG. 16A. Electronics capsule 850 may be mounted in any orientation in addition to the orientation shown. In this embodiment, a sheet of piezoelectric film is joined to a nonconductive flexible sheet 860A. Conductive leads are deposited or printed on top and bottom surfaces of this flexible sheet 860A and electrically connect the signal output from sensor 818A to circuit board 864. Conductive leads are also deposited or printed on the flexible sheet 860A to electrically connect the outputs from circuit board 864 via LED leads 828A to the LED 826 of FIG. 16A. The electronics capsule 850 as shown in this embodiment is mounted with its flat lip 876 of the base 852 flush with the upper surface of the sole of the shoe.

The circuitry involved has been reduced in size so that the circuit and LED can be operated for extended periods of time with only two batteries in series. In one test, 790,000 flashes of the LED were achieved using only standard watch batteries.

Additionally, the circuitry, as shown for example in FIG. 12, is designed so that when the LED is not lit or flashing, the current, i.e., power consumption, is insignificant. Such a low power consumption avoids the necessity of including an ON-OFF switch in the circuit in order to extend battery life.

In an alternative configuration, a solar cell or solar cell array and/or a rechargeable battery could be substituted for the battery.

Referring to FIG. 18 or 18A, the electronics capsule 850 forms a tightly sealable capsule into which the tongue 862 of the flexible sheet 860 or 860A, circuit board 864, and one or more batteries 822 fit. The base of the capsule 852 has a slot 856 through which the tongue 862 intrudes in order to reach the interior of the capsule 850 enabling the circuit board 864 to make electrical contact with the conductive leads deposited on the flexible sheet 860 or 860A. The electronics capsule 850 may be mounted in any orientation in addition to the orientation shown.

The threads 872 on base 852 mate with corresponding threads (not shown in FIG. 18) on cap 866, which in conjunction with sealing rings 858 enable the capsule 850 to be tightly sealed. This seal can be a waterproof seal. Optionally, the entire capsule can be encapsulated in, for example a polymer, to ensure a waterproof seal and to prevent tampering with the circuitry contained therein.

Included within the electronics capsule 850 is a contact spring 854 mounted on the base 852. This contact spring 854 electrically connects the outer case of the batteries 822 to the circuit board 864.

A cross-sectional view of an assembled electronics capsule 850 is shown in FIG. 19. The electronics capsule 850, when assembled, comprises a lower sealing ring 858 which sits on the lip 876 of base 852; the ring 863 of flexible sheet 860 (or 860A, not shown) fits over base 852 and contacts the upper surface of the lower sealing ring 858; tongue 862 fits through slot 856; upper sealing ring 858 is placed over the base 826 and contacts the upper surface of ring 863; a circuit board 864 and one or more batteries 822 are placed in the center cavity 878 of the base 852; a contact spring 854 fits into a slot formed in the side of the base 852, and cap 866 is screwed onto and threadably mates with base threads 872.

Grips 868 are formed in the cap 866 to enable the cap to be grasped and unthreaded for access to the internal components. Thus, the batteries, circuit board or flexible sheet and impact sensor can be readily replaced.

The capsule is sealed by the compression of the upper and lower sealing rings 858 between the base 852, the ring 863 of the flexible sheet 860 (or 860A, not shown), and the cap 866. The base thread 872 mates with the cap thread 870. The length of these threads are designed to ensure that the proper pressure is applied to ring 863 and sealing rings 858 to guard against moisture, sweat, bacteria, dust and/or dirt from seeping onto the electronics capsule 850.

Typically, two batteries 822 are used in series to provide power to operate the circuitry and the light emitting device or devices. The outer case, negative electrode 823 of the upper battery is electrically connected by physical contact with contact spring 854 to the circuit board 864. The positive electrocle 824 of the upper battery is electrically and physically in contact with the negative electrode 823 of the lower battery 822. The positive electrode 824 of the lower battery 822 is physically and eletrically in contact with circuit board 864.

Conductive leads 862L deposited or printed on the tongue 862 and the flexible sheet 860 (or 860A, not shown) electrically contact circuit board 864 and thus connect the piezoelectric impact sensor 818 (or 818A, not shown) and the LED leads 828 (or 828A, not shown) and LED 826 to the circuitry located on the circuit board 864. The circuit board 864 may be keyed to ensure that the proper electrical connections are made.

Figure 20:
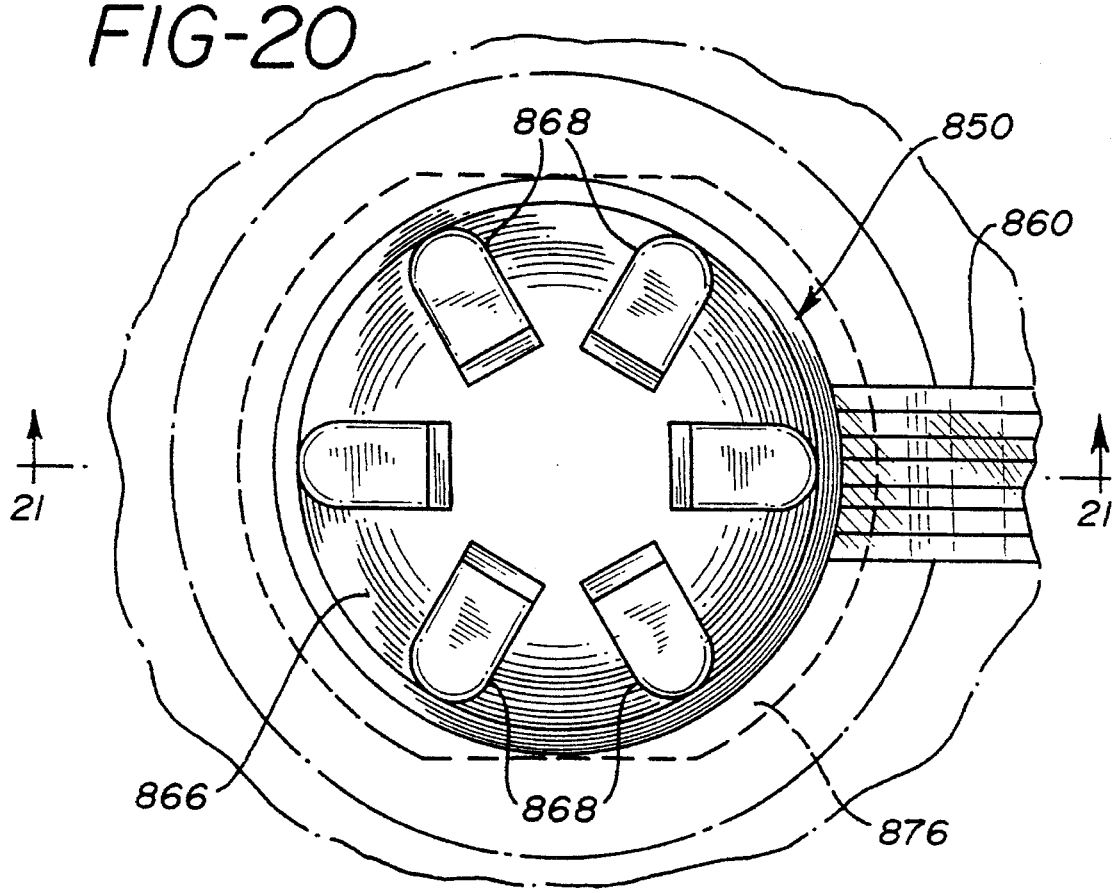
FIG. 20 shows a top plan view of the cap of the electronics capsule of FIG. 18.
Figure 21:
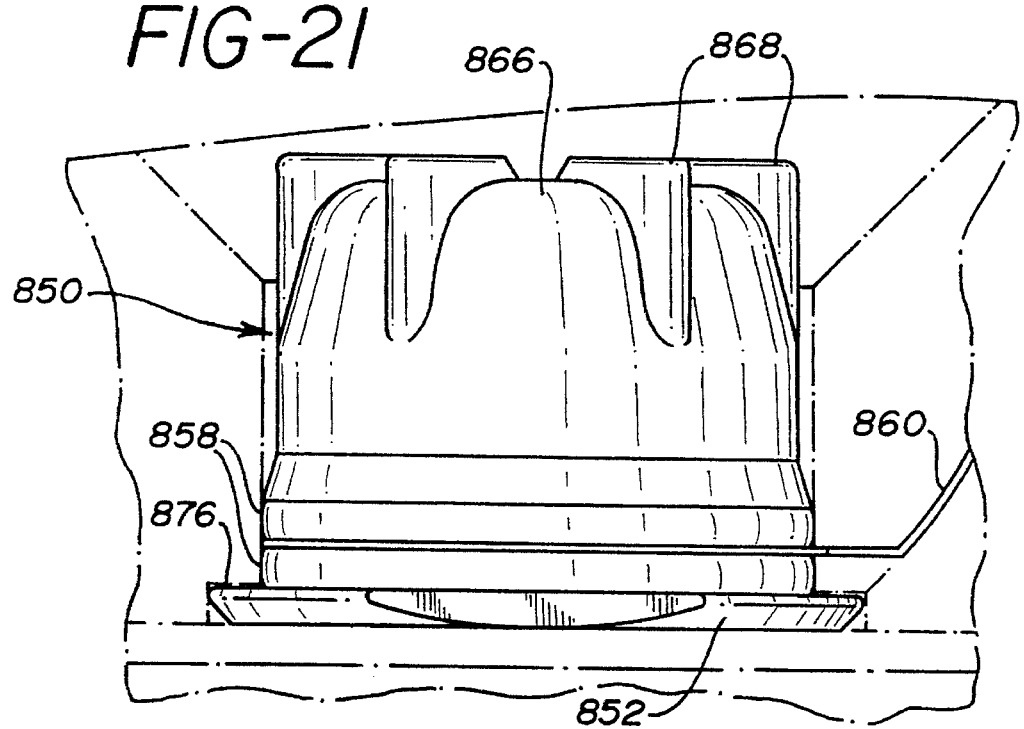
FIG. 21 shows a side plan view of the electronics capsule of FIG. 18.

FIG. 20 is a top plan view of the cap 866 of the electronics capsule 850. FIG. 21 shows a side plan view of the electronics capsule 850 with the cap 866 threaded onto the base 852 and sealing rings 858 sealing the flexible sheet 860 therebetween.

The curved surface of the cap 866 with flat topped grips 868 is designed to maximize the strength of the capsule so that sudden impacts by the wearer of the shoe will not crack, shatter or damage the capsule nor cause the capsule to rise or protrude from its cavity. In addition, the plurality of grips spaced equidistantly about the top circumference of the cap, facilitate easy unthreading of the cap so that the internal components can be replaced and/or repaired.

FIG. 22 diagramically illustrates the critical angles involved in positioning LED 826 in the light chamber 844 of the light unit 840 as shown in FIGS. 16 and 17. In this embodiment, the LED 826 is positioned to maximize the light energy that falls on the lens 842 so as to maximize the light or the image projected to the rear of the shoe.

Figure 23:
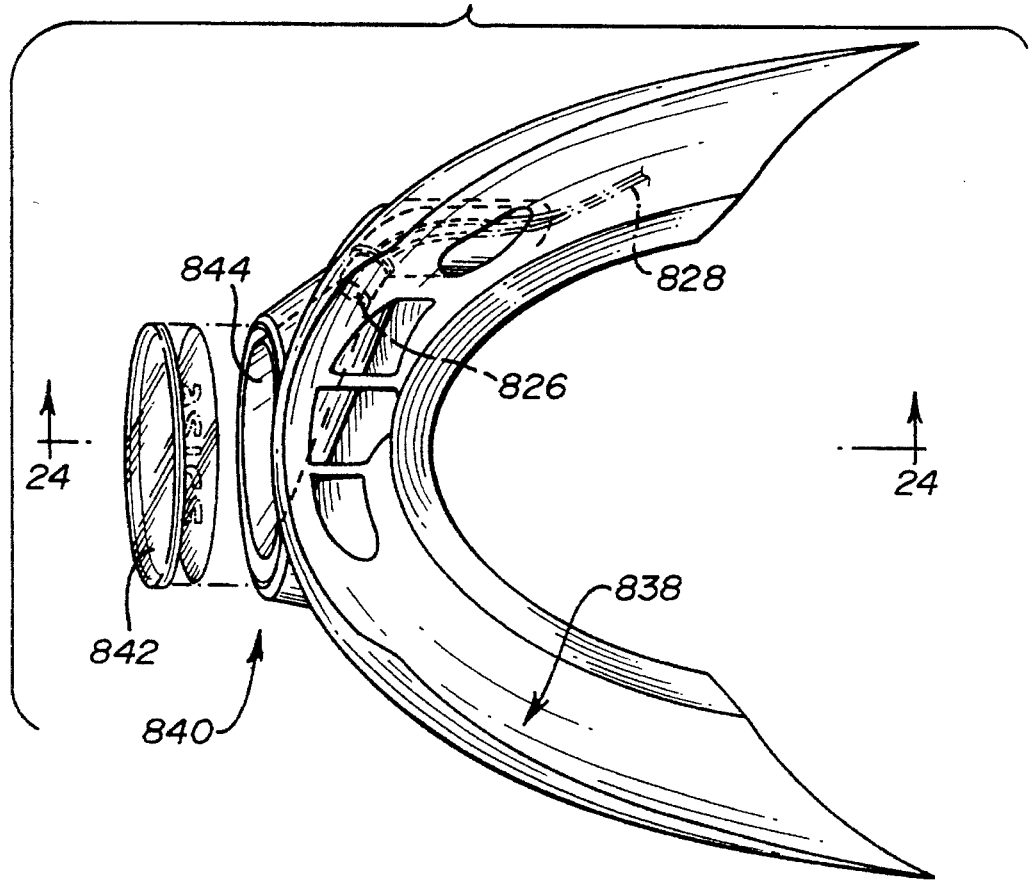
FIG. 23 is a partially exploded top plan view of a section of the heel of the shoe of FIG. 15 with a portion of the illumination means shown in phantom.
Figure 24:
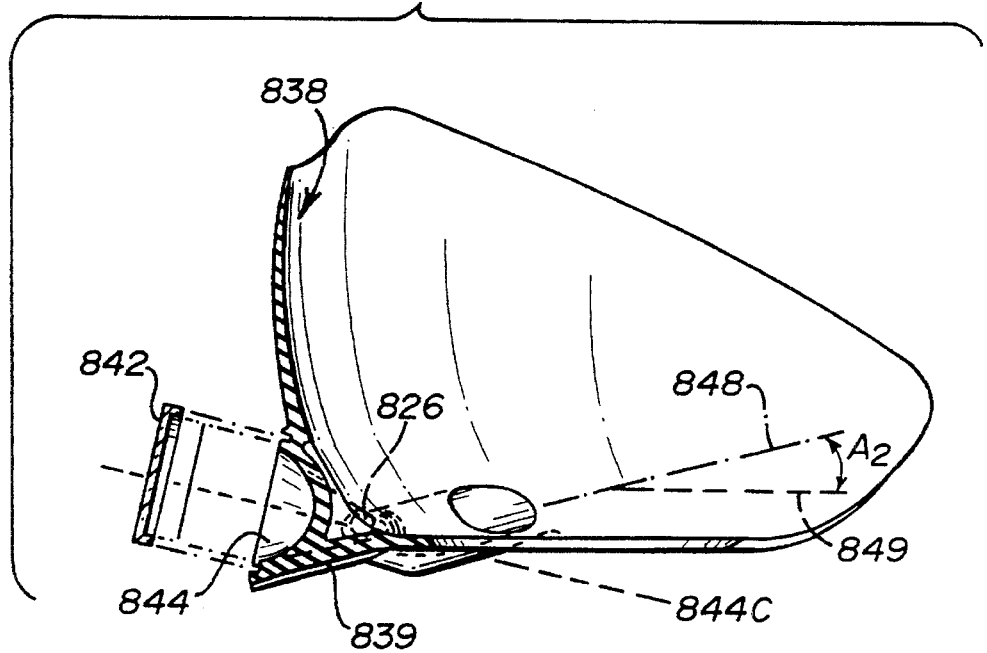
FIG. 24 shows a cross-sectional view of a portion of the heel of the shoe of FIG. 15 illustrating the location and configuration of the light chamber and light emitting diode.

Considerable effort was devoted to identifying the best angle for placement of an LED in a light chamber in order to maximize the light transmitted from the lens while fitting this light chamber and LED into the heel section (heel counter) of a shoe without adding excessive and obtrusive bulk. FIGS. 22, 23, and 24 reflect a solution to this problem.

FIG. 23 is a partial cutaway and phantom view of a section of the heel of the shoe of FIG. 15 showing the angular and spatial location of LED 826 and LED leads 828 with respect to the light chamber 844 and the lens 842.

FIG. 24 illustrates a cross-sectional side view through the heel of FIG. 23. This side view further shows the placement of LED 826 with respect to light chamber 844 and lens 842.

The design of the light chamber provides for uniform illumination of lens 842 by LED 826, without the LED 826 being mounted directly behind, i.e., perpendicular to, the lens 842. As is apparent from FIG. 22, the LED center line $826C_L$ is offset by an angle A1 from the light chamber center line $844C_L$. In one embodiment, these center lines in plan view are offset 4mm to achieve maximum illumination of lens 842 while minimizing the bulk of the light chamber in the heel counter of a shoe.

Referring to FIG. 24, minimizing the center line 848 offset relative to the datum line 849 of the heel counter is a critical factor in minimizing the bulk of the heel counter 839. An angle A2 of about 15 degrees minimizes the bulk of the heel counter 839 when light chamber 844 is incorporated into the shoe. Placing the light chamber higher up the heel 838 results in external heel moldings that are larger than necessary, an unacceptable angle for lens 842 in order to provide acceptable rearward visibility and a light chamber that protrudes excessively from the heel.

In another embodiment of the invention, referring to FIG. 2, a ball 930 is molded in a translucent synthetic rubber material around a central cavity 932 containing a battery-powered light emitting unit 934. The unit 934 comprises a piezoelectric impact sensor 936, preferably of PVDF similar to the piezoelectric impact sensor 218 of FIG. 1. The piezoelectric impact sensor 936 is electrically connected to a ball circuit similar to the circuit 220 of FIG. 3. The ball circuit is powered by a battery pack 940 similar to the battery pack 222 of FIG. 3. The difference is that the ball circuit turns on two LEDs 942 both similar to the LED 226 of FIG. 1. The LEDs 942 are positioned so as to emit light outwards from the central cavity 932 in generally opposite directions.

In operation, each time the ball 930 impacts a hard surface, e.g. each time it is bounced, the piezoelectric impact sensor 936 is stressed, and so produces a pulse of electrical energy which triggers a monostable circuit that allows both LEDs 942 to light for a predetermined time period. Since the LEDs 942 emit light in generally opposite directions, one or the other LED tends to be visible regardless of the direction from which the ball 930 is viewed.

The fact that the ball 930 is molded in a translucent (as opposed to a fully transparent) material means that the emitted light tends to be diffused, and the components making up the light emitting unit 934 (i.e. the piezoelectric impact sensor 936, the ball circuit, the battery pack 940 and the LEDs 942) are not clearly and individually visible as separate components.

It should be noted that the LED 326 of the shoes of the present invention or the LEDs 942 of the ball of the present invention can be replaced by sound-emitting devices. Similarly, the circuitry can be modified so that both the LED and the sound-emitting device can be incorporated in the same product.

Referring to FIG. 9, it is seen that the present invention can also be used in connection with a fishing lure 986, comprising a piezoelectric impact sensor a circuit 920, a battery pack 922 and an LED 926. The lure 986 can be shaped or molded to resemble a fish having fins 988 and a tail 990. Additionally, the fishing lure may comprise a fish shape with optical fibers 992 conducting light from the LED 926 to, e.g., the fins and/or tail (or even eyes) of the fish-shaped lure. In operation, impacts from jerks on the fishing line or the like are sensed by the piezoelectric impact sensor 918, these impacts generate a trigger signal to circuit 920 which in turn lights/flashes the LED 926 for a preselected time period.

It will be understood that various changes in the details, materials, and arrangements of parts may be made by those skilled in the art within the principle and scope of the invention.

What is claimed is

1. A shoe that lights, comprising a sole;

pressure sensor means incorporated within the sole comprising piezoelectric material for generating trigger signals upon application of pressure to the material, the sole imparting pressure to the material when impressed against a surface;

a light emitting diode (LED);

power means for powering the LED;

monstable multivibrator circuit means interconnecting the pressure sensor means, the LED and the power means, wherein the circuit means responds to the trigger signals to control the power means to power the LED in response to the pressure imparted by the sole on the material;

wherein the circuit means comprises input means for accepting the trigger signals from the pressure sensor means and transmitting the trigger signals to the circuit means, the input means including sensitivity resistive means across which the trigger signals are applied for controlling the sensitivity of the piezoelectric material;

output leads for transmitting a signal generated by the circuit means to the LED, including a first resistive means for limiting the current through the LED;

a second resistive means coupled with a capacitive means to form a resistive-capacitive (R-C) combination timing means for determining the length of time the signal is generated by circuit means; and means for applying the voltage developed across the capacitive means of the R-C timing circuit means to the input of the monostable multivibrator circuit means.

2. The shoe of claim 1, wherein the LED is positioned at the rear of the shoe and is visible from behind the shoe.

3. The shoe of claim 1, wherein the LED is positioned within the shoe and includes optic fibers leading from the LED to the outside of the shoe to conduct light from the LED to the outside of the shoe.

4. The shoe of claim 3, wherein the optic fibers include a plurality of notches for permitting the emission of light therefrom.

5. The shoe of claim 1, wherein the pressure sensor means comprises a plurality of pressure sensors.

6. The shoe of claim 1, wherein the output means comprises a plurality of LEDs.

7. The shoe of claim 6, wherein the plurality of LED's are arranged sequentially in the upper of the shoe to form a bar graph display of information produced by the pressure sensor means and the circuit means.

8. The shoe of claim 7, wherein the circuit means comprises a microprocessor means to provide preprogrammed control of the plurality of LEDs.

9. A lighted shoe comprising a sole;

pressure sensor means incorporated within the sole comprising a polyvinylidene fluoride (PVDF) polymeric piezoelectric material for generating trigger signals upon application of pressure to the material;

the sole imparting pressure to the material when impressed against a surface;

a light emitting diode (LED);

a battery for powering the LED;

a monostable multivibrator circuit means interconnecting the pressure sensor means, the LED and the battery, wherein the circuit means responds to the trigger signals to control the battery to power the LED in response to the pressure imparted by the sole on the material;

wherein the circuit means comprises input means for accepting the trigger signals from the pressure sensor means and transmitting the trigger signals to the circuit means, the input means including a sensitivity resistive means across which the trigger signals are applied;

output leads for transmitting a signal generated by the circuit means to the LED, including a first resistive means for limiting the current through the LED;

a second resistive means coupled with a capacitive means to form a resistive-capacitive (R-C) combination timing means for determining the length of time the signal is generated by the circuit means;

means for applying the voltage developed across the capacitive means of the R-C timing circuit means to the input of the monostable multivibrator circuit means;

a sealed capsule incorporated within the sole for encapsulating the battery and circuit means, the capsule comprising a base having a cylindrical portion and a lip thereon;

a lower sealing ring sized to receive the cylindrical portion of the base and to coact with the lip;

means for releasable accepting leads from the pressure sensor means;

an upper sealing ring sized to receive the cylindrical portion of the base, the upper sealing ring and the lower sealing ring co-acting to position and hold leads from the pressure sensor means and the LED and to seal the capsule;

circuit board means for supporting the circuit means, the circuit board means sized to be accepted within the cylindrical portion of the base, the circuit board means being in electrical contact with the leads and the battery;

the battery sized to be received within the cylindrical portion of the base, the battery being in electrical contact with the circuit means on the circuit board means;

a contact spring means positioned within the cylindrical portion of the base, one end of the contact spring means contacting the negative terminal of one battery and the other end contacting the circuit means on the circuit board means; and a cap threadably attachable to the base, the cap and the base co-acting to close and seal the capsule.

* * * * *